US009315810B2

(12) United States Patent
Matsuda et al.

(10) Patent No.: US 9,315,810 B2
(45) Date of Patent: Apr. 19, 2016

(54) OLIGONUCLEOTIDE DERIVATIVE, OLIGONUCLEOTIDE DERIVATIVE-CONTAINING PHARMACEUTICAL COMPOSITION FOR TREATMENT AND PHARMACEUTICAL COMPOSITION FOR DIAGNOSIS, AND OLIGONUCLEOTIDE DERIVATIVE FOR REGULATION OF MIRNA FUNCTION

(75) Inventors: Akira Matsuda, Hokkaido (JP); Mayumi Takahashi, Hokkaido (JP)

(73) Assignee: National University Corporation Hokkaido University, Hokkaido (JP)

( * ) Notice: Subject to any disclaimer, the term of this patent is extended or adjusted under 35 U.S.C. 154(b) by 0 days.

(21) Appl. No.: 14/123,562

(22) PCT Filed: Jun. 1, 2012

(86) PCT No.: PCT/JP2012/064276
§ 371 (c)(1),
(2), (4) Date: Dec. 3, 2013

(87) PCT Pub. No.: WO2012/165616
PCT Pub. Date: Dec. 6, 2012

(65) Prior Publication Data
US 2014/0128347 A1  May 8, 2014

(30) Foreign Application Priority Data
Jun. 3, 2011 (JP) .................................. 2011-125734

(51) Int. Cl.
*C12N 15/113* (2010.01)
*A61K 31/7088* (2006.01)
*A61K 31/713* (2006.01)

(52) U.S. Cl.
CPC .......... *C12N 15/113* (2013.01); *A61K 31/7088* (2013.01); *A61K 31/713* (2013.01); *C12N 2310/113* (2013.01); *C12N 2310/315* (2013.01); *C12N 2310/3235* (2013.01); *C12N 2310/351* (2013.01)

(58) Field of Classification Search
None
See application file for complete search history.

(56) References Cited

U.S. PATENT DOCUMENTS

2005/0130923 A1* 6/2005 Bhat et al. ..................... 514/44
2007/0269889 A1* 11/2007 Leake et al. .................. 435/375

OTHER PUBLICATIONS

Bonci "MicroRNA-21 as Therapeutic Target in Cancer and Cardiovascular Disease." Cardiovascular Drug Discovery, 2010, 5, 156-161.
Broderick et al. "MicroRNA Therapeutics." Gene Therapy (2011) 18, 1104-1110.
Cummins et al. "Characterization of fully 2'-modified oligoribonucleotide hetero and homoduplex hybridization and nuclease sensitivity." Nucleic Acids Research, 1995, vol. 23, No. 11 2019-2024.
Dande et al. "Improving RNA Interference in Mammalian Cells by 4'-Thio-Modified Small Interfering RNA (siRNA): Effect on siRNA Activity and Nuclease Stability When Used in Combination with 2'-O-Alkyl Modifications." J. Med. Chem. 2006, 49, 1624-1634.
Hoshika et al. "Synthesis and physical and physiological properties of 4'-thioRNA: application to post-modification of RNA aptamer toward NF-kB." Nucleic Acids Research, 2004, vol. 32, No. 13 3815-3825.
Judge et al. "Design of Noninflammatory Synthetic siRNA Mediating Potent Gene Silencing in Vivo." Molecular Therapy vol. 13, No. 3, Mar. 2006.
Lanford et al. "Therapeutic Silencing of MicroRNA-122 in Primates with Chronic Hepatitis C Virus Infection." Science 327, 198, 2010.
Morrisey "The magic and mystery of miR-21." The Journal of Clinical Investigation, vol. 120, No. 11, Nov. 2010.
Musso et al. "Emerging Molecular Targets for the Treatment of Nonalcoholic Fatty Liver Disease." Annu. Rev. Med. 2010, 61:375-92.
Shan et al. "Reciprocal Effects of Micro-RNA-122 on Expression of Heme Oxygenase-1 and Hepatitis C Virus Genes in Human Hepatocytes." Gastroenterology 2007; 133: 1166-1174.
Takahashi et al. "Synthesis and characterization of 2'-modified-4'-thioRNA: a comprehensive comparison of nuclease stability." Nucleic Acids Research, 2009, vol. 37, No. 4, 1353-1362.
Takahashi et al. "Intracellular stability of 2'_OMe-4'-thioribonucleoside modified siRNA leads to long-term RNAi effect." Nucleic Acids Research, 2012m vol. 40, No. 12, 5787-5793.

* cited by examiner

*Primary Examiner* — Tracy Vivlemore
(74) *Attorney, Agent, or Firm* — K&L Gates, LLP; Louis Cullman; Michelle Glasky Bergman

(57) ABSTRACT

An oligonucleotide derivative comprises repeating structural units represented by the following general formula (wherein B represents adenine, guanine, cytosine, or uracil; X represents a sulfur atom or an oxygen atom; n represents an integer of 6 to 60; and B and X are independently represented in each of the repeating structural units), wherein X is a sulfur atom in at least one of the repeating structural units represented by the general formula:

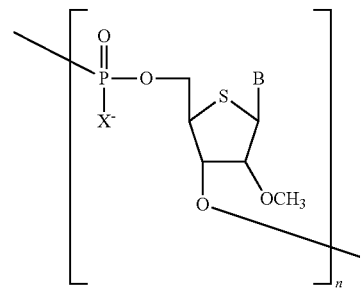

7 Claims, 13 Drawing Sheets

FIG. 1

SEQUENCES AND Tm VALUES OF AMOs 21

| | AMOs | SEQUENCES | Tm VALUES (°C) AGAINST miRNA-21 (COMPLEMENTARY RNA) |
|---|---|---|---|
| | 32-MER SERIES | | |
| SEQ ID NO:4 | AMO21(32)_Me | 5'-UCUUAUCAACAUCAGUCUGAUAAGCUAACCUU | 58.0 ± 0.1 |
| SEQ ID NO:4 | AMO21(32)_SMe | 5'-UCUUAUCAACAUCAGUCUGAUAAGCUAACCUU | 62.1 ± 1.0 |
| | 22-MER SERIES | | |
| SEQ ID NO:3 | AMO21_Me_PO | 5'-UCAACAUCAGUCUGAUAAGCUA | 59.9 ± 0.2 |
| SEQ ID NO:3 | AMO21_FMe_PO | 5'-UCAACAUCAGUCUGAUAAGCUA | 67.9 ± 0.2 |
| SEQ ID NO:3 | AMO21_SMe_PO | 5'-UCAACAUCAGUCUGAUAAGCUA | 64.1 ± 0.1 |
| SEQ ID NO:3 | AMO21_SFMe_PO | 5'-UCAACAUCAGUCUGAUAAGCUA | 71.1 ± 0.1 |
| SEQ ID NO:5 | AMO21_SMe_PS | 5'-U$_S$C$_S$A$_S$A$_S$C$_S$A$_S$U$_S$C$_S$A$_S$G$_S$U$_S$C$_S$U$_S$G$_S$A$_S$U$_S$A$_S$A$_S$G$_S$C$_S$U$_S$A | 63.4 ± 0.5 |

N$_S$N : PHOSPHOROTHIOATE LINKAGE

FIG. 2

SEQUENCES AND Tm VALUES OF AMOs 122

| | AMOs | SEQUENCES | Tm VALUES (°C) AGAINST miRNA-122 (COMPLEMENTARY RNA) |
|---|---|---|---|
| SEQ ID NO:5 | AMO122_Me_PO | 5'-ACAAACACCAUUGUCACACUCCA | 62.9 ± 0.06 |
| SEQ ID NO:5 | AMO122_Me_PS | 5'-A$_s$C$_s$A$_s$A$_s$A$_s$C$_s$A$_s$C$_s$C$_s$A$_s$U$_s$U$_s$G$_s$U$_s$C$_s$A$_s$C$_s$A$_s$C$_s$U$_s$C$_s$C$_s$A | 58.0 ± 0.10 |
| SEQ ID NO:5 | AMO122_SMe_PO | 5'-ACAAACACCAUUGUCACACUCCA | 65.8 ± 0.12 |
| SEQ ID NO:5 | AMO122_SMe_PS | 5'-A$_s$C$_s$A$_s$A$_s$A$_s$C$_s$A$_s$C$_s$C$_s$A$_s$U$_s$U$_s$G$_s$U$_s$C$_s$A$_s$C$_s$A$_s$C$_s$U$_s$C$_s$C$_s$A | 64.8 ± 0.06 |

N$_s$N : PHOSPHOROTHIOATE LINKAGE

EVALUATION OF ACTIVITIES OF AMOs 122 (AFTER 24 HOURS)

EVALUATION OF ACTIVITIES OF CONJUGATED
AMOs 122 (AFTER 24 HOURS)

EVALUATION OF ACTIVITIES OF CONJUGATED
AMOs 122 (AFTER 72 HOURS)

OLIGONUCLEOTIDE DERIVATIVE, OLIGONUCLEOTIDE DERIVATIVE-CONTAINING PHARMACEUTICAL COMPOSITION FOR TREATMENT AND PHARMACEUTICAL COMPOSITION FOR DIAGNOSIS, AND OLIGONUCLEOTIDE DERIVATIVE FOR REGULATION OF MIRNA FUNCTION

CROSS REFERENCE TO RELATED APPLICATIONS

This application is a national phase of PCT/JP2012/064276 filed on Jun. 1, 2012 which claims priority to Japanese Patent Application JP2011-125734 filed on Jun. 3, 2011, the entire disclosures of which are incorporated by reference herein.

TECHNICAL FIELD

The present invention relates to an oligonucleotide derivative, a pharmaceutical composition for treatment and a pharmaceutical composition for diagnosis that include the oligonucleotide derivative, as well as to an oligonucleotide derivative for inhibiting miRNA function.

BACKGROUND ART

In recent years, due to the discovery of RNA interference (RNAi), the advancement of transcriptome analysis methods, and the like, research on RNA has been dramatically expanded. It has been shown that RNA regulates many biologically important functions, and associations between RNA and various diseases including cancer have been pointed out.

Studies on cancer treatment by regulation of RNA function have been vigorously conducted and research and development of RNA-targeting pharmaceuticals have been widely carried out. Above all, RNA regulation method using a nucleic acid is based on the Watson-Crick type base pair formation and uses a nucleic acid having a sequence specific to a target RNA. Such an RNA regulation method directly regulates RNA, thereby allowing the adjustment of cellular function.

In recent years, as an RNA regulation method using a nucleic acid, methodologies such as antisense method and RNAi method have been established. In addition, studies on nucleic acid medicines for inhibiting the function of microRNA (hereinafter referred to as miRNA) have been advanced (Non Patent Literature 1).

Nucleic acid medicines produced by application of RNA regulation method using a nucleic acid have problems to be solved, such as (1) the loss of effect due to decomposition by nuclease present inside and outside cells, (2) thermal instability of a double-stranded higher order structure, (3) targeting of cells and tissues, and (4) occurrence of side effects due to natural immune response.

In order to overcome these problems, in the creation of nucleic acid medicines, studies have been conducted to provide functions such as resistance against nuclease, thermal stability of the double-stranded higher order structure, and an ability to avoid natural immune response by performing some chemical modification on a nucleic acid. It has been reported that 2'-O-methyl RNAs obtained by the methylation of a hydroxyl group at position 2' of the sugar moiety of a nucleic acid have nuclease resistance, thermal stability, and the ability to avoid a natural immune response (Non Patent Literature 2 and 3). In addition, it has been reported that 4'-thioRNA obtained by the substitution of an oxygen atom at position 4' of a furanose ring of a nucleoside sugar moiety with a sulfur atom has a nuclease resistance and thermal stability (Non Patent Literature 4).

CITATION LIST

Non Patent Literature

Non Patent Literature 1: Robert E. Lanford et al., Science, 327, 198-201 (2010).
Non Patent Literature 2: Commins L. L. et al., Nucleic Acids Res. 23, 2019-2024 (1995).
Non Patent Literature 3: Judge A. D. et al., Mol. Ther. 13, 494-505 (2006).
Non Patent Literature 4: Hoshika S., Minakawa N. and Matsuda A., Nucleic Acids Res. 32, 3815-3825 (2004).

SUMMARY OF INVENTION

Technical Problem

However, the 2'-O-methyl RNAs described in Non Patent Literature 2 and 3 are not considered to be sufficiently stable in in vivo environments and also are still problematic in terms of persistence of effect. In addition, although the 4'-thioRNA described in Non Patent Literature 4 has nuclease resistance, the development of modified RNAs having more excellent nuclease resistance has been desired in order to use in vivo as nucleic acid medicines.

The present invention has been accomplished in view of the above circumstances, and the objectives of the present invention are to provide an oligonucleotide derivative having excellent effect persistence enough for in vivo use and thermal stability, a pharmaceutical composition for treatment and a pharmaceutical composition for diagnosis that include the oligonucleotide derivative, as well as an oligonucleotide derivative for inhibiting miRNA function.

Solution to Problem

In order to achieve the above objectives, an oligonucleotide derivative according to a first aspect of the present invention comprises repeating structural units represented by the following general formula:

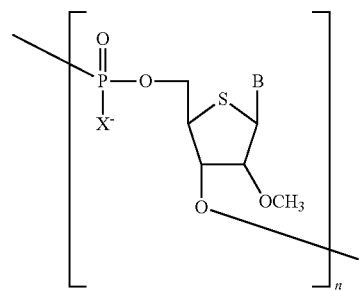

(wherein B represents adenine, guanine, cytosine, or uracil; X represents a sulfur atom or an oxygen atom; n represents an integer of 6 to 60; and B and X are independently represented in each of the repeating structural units), wherein X represents a sulfur atom in at least one of the repeating structural units represented by the general formula.

X may represent a sulfur atom in all of the repeating structural units represented by the general formula.

At least one ligand may be bound to the 5' end, the 3' end, or both the 5' end and the 3' end of the oligonucleotide derivative.

The oligonucleotide derivative may comprise a sequence complementary to the entire sequence or a partial sequence of a miRNA.

The miRNA may be miRNA-21.

The miRNA may be miRNA-122.

A pharmaceutical composition for treatment according to a second aspect of the present invention includes the oligonucleotide derivative.

The pharmaceutical composition for treatment may inhibit miRNA function.

A pharmaceutical composition for diagnosis according to a third aspect of the present invention includes the oligonucleotide derivative.

An oligonucleotide derivative for inhibiting miRNA function according to a fourth aspect of the present invention comprises repeating structural units represented by the following general formula:

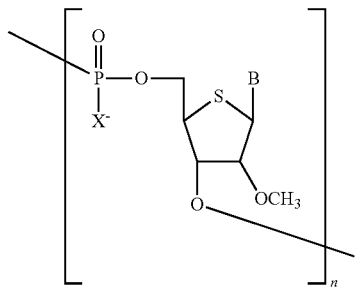

(wherein B represents adenine, guanine, cytosine, or uracil; X represents a sulfur atom or an oxygen atom; n represents an integer of 6 to 60; and B and X are independently represented in each of the repeating structural units), wherein X is a sulfur atom in at least one of the repeating structural units represented by the general formula.

X may represent a sulfur atom in all of the repeating structural units represented by the general formula.

At least one ligand may be bound to the 5' end, the 3' end, or the 5' end and the 3' end of the oligonucleotide derivative.

The oligonucleotide derivative may comprise a sequence complementary to the entire sequence or a partial sequence of a miRNA.

The miRNA may be miRNA-21.

The miRNA may be miRNA-122.

Advantageous Effects of Invention

The present invention can provide an oligonucleotide derivative having excellent effect persistence enough for in vivo use and thermal stability, a pharmaceutical composition for treatment and a pharmaceutical composition for diagnosis that include the oligonucleotide derivative, as well as an oligonucleotide derivative for inhibiting miRNA function.

BRIEF DESCRIPTION OF DRAWINGS

FIG. 1 is a view depicting sequences and Tm values of individual unconjugated AMOs 21;

FIG. 2 is a view depicting sequences and Tm values of individual unconjugated AMOs 122;

DESCRIPTION OF EMBODIMENTS

Figure 3:
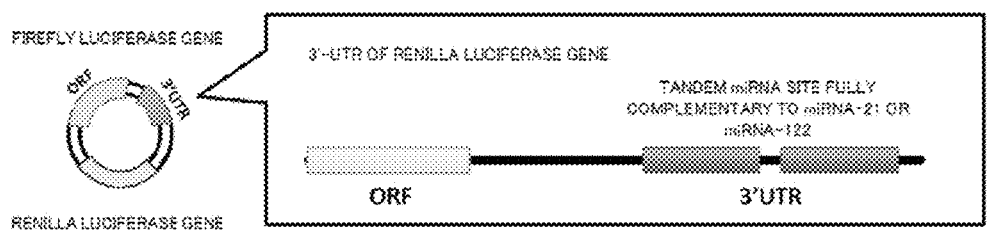
FIG. 3 is a view illustrating a reporter vector used to evaluate an inhibitory effect of each AMO on miRNA.

Embodiments of the present invention will be described in detail below.

(1. Oligonucleotide Derivative)

First, a detailed description will be given of the structure of an oligonucleotide derivative according to the present invention.

The oligonucleotide derivative according to the present invention comprises repeating structural units represented by the following general formula (1). In the present specification, the term oligonucleotide derivative means that a nucleotide in an oligonucleotide is chemically modified as represented by the following general formula (1). The oligonucleotide derivative according to the present invention also includes an oligonucleotide derivative in which at least one nucleotide in an oligonucleotide is chemically modified as represented by the following general formula (1). In this case, an oligonucleotide derivative to be preferably used is an oligonucleotide derivative in which 50% or more of nucleotides in the entire length of the oligonucleotide are chemically modified as represented by the following general formula (1):

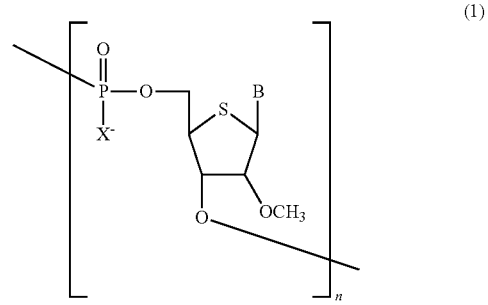

In the general formula (1), B represents adenine, guanine, cytosine, or uracil. Structures and abbreviation codes of the individual bases are indicated in the following formulas:

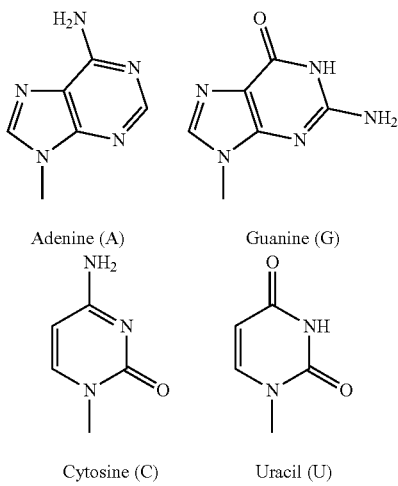

Adenine (A)  Guanine (G)  Cytosine (C)  Uracil (U)

In the general formula (1), X represents a sulfur atom or an oxygen atom. In the present specification, an oligonucleotide derivative in which X represents a sulfur atom is referred to as PS, and an oligonucleotide derivative in which X represents an oxygen atom is referred to as PO. The PS and the PO, respectively, are represented by respective formulas below:

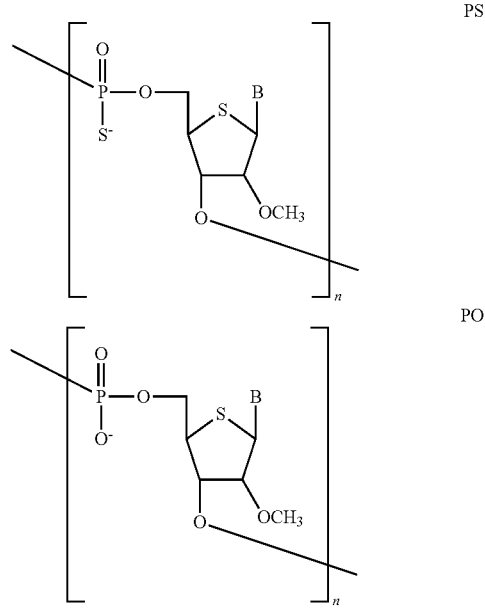

PS

PO

In the general formula (1), n represents the number of the repeating structural units represented by the general formula (1), namely, the number of monomers in the oligonucleotide derivative according to the present invention, which is an integer of 6 to 60. The number of the monomers (=n) will be described below.

In the general formula (1), B and X are independently represented in each of the repeating structural units. In other words, in the oligonucleotide derivative, repeating structural units having different B and X may be present together. For example, in a single repeating structural unit included in the oligonucleotide derivative, B may represent adenine and X may represent a sulfur atom, whereas, in another repeating structural unit in the same oligonucleotide derivative, B may represent guanine and X may represent an oxygen atom, and in still another repeating structural unit in the same oligonucleotide derivative, B may represent cytosine and X may represents an oxygen atom.

In the oligonucleotide derivative according to the present invention, X represents a sulfur atom in at least one of the repeating structural units represented by the general formula (1). In other words, the oligonucleotide derivative according to the present invention includes at least one repeating structural unit represented by the general formula (1) in which X represents a sulfur atom, namely, PS.

In the oligonucleotide derivative according to the present invention, X may represent a sulfur atom in all of the repeating structural units represented by the general formula (1). In other words, all of the repeating structural units represented by the general formula (1) included in the oligonucleotide derivative may be PS. The oligonucleotide derivative comprising PS, namely, phosphorothioate has excellent effect persistence enough for in vivo use and thermal stability and therefore can be preferably used as the oligonucleotide derivative according to the present invention.

Next, a detailed description will be given of a function of the oligonucleotide derivative according to the present invention.

The oligonucleotide derivative according to the present invention can be widely used as an RNA-targeting nucleic acid (an antisense nucleic acid compound). In the present specification, the antisense nucleic acid compound means an oligonucleotide derivative comprising a sequence complementary to the entire sequence or a partial sequence of a target RNA, in which all or part of nucleotides in oligonucleotide are chemically modified. The oligonucleotide derivative according to the present invention can be used, for example, for direct regulation of mRNA, regulation of miRNA function, and the like.

When the oligonucleotide derivative according to the present invention is used for direct regulation of mRNA, the oligonucleotide derivative to be used is an oligonucleotide derivative comprising a sequence complementary to the entire sequence or a partial sequence of a target mRNA. In this case, for example, due to a mechanism as below, translational inhibition occurs. For example, during a splicing process from pre-mRNA to mRNA, the oligonucleotide derivative according to the present invention binds to the pre-mRNA to cause inhibition of cap formation, splicing inhibition, cleavage by RNase, adenylation inhibition, and the like. In addition, for example, during the process of translation from mRNA, by bonding of the oligonucleotide derivative according to the present invention to mRNA, ribosome binding inhibition (Translational Arrest) occurs. The oligonucleotide derivative according to the present invention has excellent effect persistence enough for in vivo use and thermal stability and therefore can efficiently directly regulate mRNA.

When the oligonucleotide derivative according to the present invention is used for direct regulation of mRNA, an oligonucleotide derivative of 6- to 60-mers is preferably used, and an oligonucleotide derivative of 15- to 25-mers is more preferably used. An oligonucleotide derivative having a length that allows the advantageous effects of the present invention to be obtained can be appropriately selected. Additionally, it should be understood that the present invention also includes aspects of a method for directly regulating mRNA using the oligonucleotide derivative according to the present invention.

The oligonucleotide derivative according to the present invention can be preferably used, for example, for regulation of miRNA function.

In recent years, it has been pointed out that miRNA regulates biologically importance functions such as cell proliferation and reproductive function and has associations with various diseases. Examples of known physiological functions regulated by miRNA include differentiation, cell proliferation, fertility, apoptosis, metabolism, hematopoiesis, cardiogenesis, morphogenesis, insulin secretion, and signal transduction. Accordingly, miRNA plays an important role in the presence of cells, and it is known that regulation failure of gene expression due to miRNA expression abnormalities or the like causes diseases such as cancer.

In recent years, about 900 miRNAs have been identified. Examples of miRNAs up-regulated and down-regulated in various cancers are listed below (Table 1).

which is hereinafter referred to as AMO). When an AMO according to the present invention comprises a sequence complementary to a partial sequence of a miRNA, a sequence allowing the present invention to be effective can be appropriately selected as the sequence of the AMO.

When the oligonucleotide derivative according to the present invention (hereinafter referred to as AMO according to the present invention) comprising a sequence complementary to the entire sequence or a partial sequence of a miRNA is administered, for example, in vivo, the AMO according the present invention forms double strands together with the miRNA in vivo, leading to the inhibition of function of the miRNA. The AMO according the present invention has excellent effect persistence enough for in vivo use and thermal stability and therefore can efficiently regulate miRNA function.

The AMO according the present invention can target various miRNAs, because AMOs having sequences complementary to various miRNAs can be synthesized. Examples of miRNAs that can be targeted by the AMO according the

TABLE 1

| Organ | Cancer | Up-regulated | Down-regulated |
|---|---|---|---|
| | HCA and FNH | miR-224 | let-7, 122a, 422b, 203, 200c |
| Liver | HCC | 21, 224, 10b, 221, 222, 20, 18 | 199a, 199b, 200b, 223, 122, 214, 145, 150 |
| | Cholangiocarcinomas | 21, 23a, 141, 200b, 27a | |
| | PET | miR-23a, 342, 26a, 30d, 26b, 103, 107 | 155, 326, 339, 326 |
| | Insulinomas | 203, 204, 211, | |
| Pancreas | PACC | 23a, 342, 26a, 30d, 26b, 103, 105 | 155, 326, 229, 326 |
| | Ductal adenocarcinomas | 21, 221, 181a, 155, 222, 181b, 107 | 148a, 375 |
| Esophagus | ESCC | miR-25, 424, 151 | 100, 99, 29c, 140, 205, 203, 202 |
| Stomach | Adenocarcinomas | miR-21, 223, 25, 17-5p, 125b, 181b, 106a, 107, 92, 103, 221, 93, 100, 106b | let-7, 136, 218, 212, 96, 339 |
| | Adenomas | miR-21 | let-7, 34, 127, 133b, 143 |
| Colon | Adenocarcinomas Adenocarcinomas stage II | 21, 92, 20a, 106a, 92, 223 | 145 |
| Hematopoietic tissue | CLL | miR-190, 33, 19a, 140, 123, 10b, 92, 188, 154, 217, 101, 196, 134, 141, 132, 192, 16, 15 | 181b, 220 |
| Ovary | Carcinomas | miR-200a, 200c | let-7, 100, 101, 105, 125a, 125b, 126, 133, 140, 143, 147, 199a, 199b, 224, 9, 99a |
| Breast | Carcinomas | miR-155, 21 | 125b, 145, 10b |
| Lung | NSCLC | miR-21, 191, 155, 210 | 126, 224 |
| Pituitary gland | Adenoma | miR-15, 16 | |
| Prostate | Carcinomas | miR-32, 182, 31, 26a, 200c | 520h, 494, 490, 133a, 1, 218, 220, 128a |
| Thyroid | Papillary carcinomas Anaplastic carcinomas | miR-221, 221, 146a, 181b | 125b, 26a, 30a-5p |

Names of miRNA: miR-xx (x represents numeric values; lin-4 and let-7 are exceptions). Visone, R. & Croce, C. Am J Pathol. 174, 1131-1138 (2009).

For example, miRNA-21 (SEQ ID NO: 1) is up-regulated in many cancers, such as liver cancer, pancreatic cancer, stomach cancer, breast cancer, and lung cancer (Table 1).

For example, miRNA-122 (SEQ ID NO: 2) is a miRNA specifically expressing in liver and is known to increase in embryo formation in mice to regulate the development of the liver. It has also been found that miRNA-122 is involved in the regulation of cholesterol and lipid metabolism and the replication of HCV.

The oligonucleotide derivative according to the present invention may comprise a sequence complementary to the entire sequence or a partial sequence of a miRNA. In this case, the oligonucleotide derivative can be used as a miRNA-targeting antisense nucleic acid (anti-miRNA oligonucleotide, present invention include miRNA-21, miRNA-122, miRNA-224, miRNA-10b, miRNA-221, miRNA-222, miRNA-20, miRNA-18, miRNA-23a, miRNA-141, miRNA-200b, miRNA-27a, miRNA-342, miRNA-26a, miRNA-30d, miRNA-26b, miRNA-107, miRNA-203, miRNA-204, miRNA-211, miRNA-105, miRNA-181a, miRNA-155, miRNA-181b, miRNA-25, miRNA-424, miRNA-151, miRNA-223, miRNA-25, miRNA-17-5p, miRNA-125b, miRNA-106a, miRNA-92, miRNA-103, miRNA-93, miRNA-100, miRNA-106b, miRNA-20a, miRNA-190, miRNA-33, miRNA-19a, miRNA-140, miRNA-123, miRNA-188, miRNA-154, miRNA-217, miRNA-101, miRNA-196, miRNA-134, miRNA-132, miRNA-192, miRNA-16, miRNA-15, miRNA-200a, miRNA-200c, miRNA-191, miRNA-210, miRNA-32, miRNA-182, miRNA-31, and miRNA-146a. In addition, examples of miR-NAs that can be targeted by the AMO according to the present invention include miRNAs compiled in a database at "miR-Base: the microRNA database (http://www.mirbase.org/)". Any of the miRNAs against which the present invention is effective can be appropriately selected.

In the present specification, the term miRNA function means physiological functions such as cell proliferation and regenerative function, possessed by the various miRNAs described above. Any of such miRNA functions against which the present invention is effective can be appropriately selected.

The AMO according to the present invention may comprise a sequence complementary to the entire sequence or a partial sequence of miRNA-21 so that miRNA-21 is targeted. In this case, one example of the AMO is an AMO having a sequence of SEQ ID NO: 3 (for example, AMO21_SMe_PS). A formula of repeating structural units of AMO21_SMe_PS is indicated below:

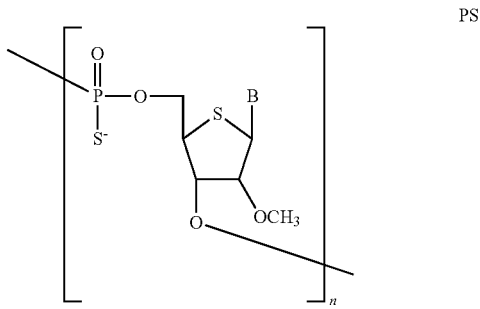

The AMO according to the present invention may comprise a sequence complementary to the entire sequence or a partial sequence of miRNA-122 so that miRNA-122 is targeted. In this case, one example of the AMO is an AMO having a sequence of SEQ ID NO: 5 (for example, AMO122_SMe_PS). A formula of repeating structural units of the AMO122_SMe_PS is indicated below:

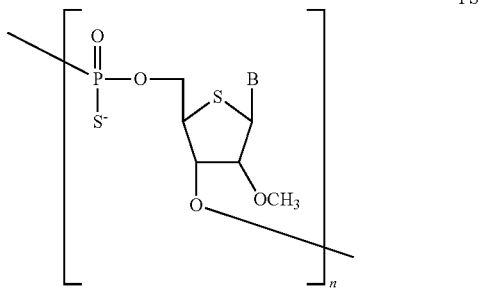

When the oligonucleotide derivative according to the present invention is used as an AMO, an AMO of 6- to 60-mers is preferably used, an AMO of 10- to 40-mers is more preferably used, and an AMO of 15- to 25-mers is still more preferably used. An AMO having a length of an oligonucleotide derivative allowing the present invention to be effective can be appropriately selected.

In the AMO according to the present invention, an additional oligonucleotide derivative of 1- to 20-mers (hereinafter referred to as an additional sequence) may be bound to the 5' end, the 3' end, or both the 5' end and the 3' end of an olignucleotide derivative comprising a sequence complementary to the entire sequence or a partial sequence of a target miRNA. For example, in an miRNA-21-targeting AMO having a sequence of SEQ ID NO: 4 (32-mers), an additional sequence of 5-mers is bound to each of the 5' end and the 3' end of AMO21_SMe_PS (22-mers). Any additional sequence allowing the present invention to be effective can be appropriately selected.

In addition, it should be understood that the present invention also includes aspects of a method for regulating miRNA function using the oligonucleotide derivative according to the present invention.

Evaluation of the inhibition of miRNA function by the oligonucleotide derivative according to the present invention can be performed, for example, as follows: when targeting miRNA-122, the oligonucleotide derivative according to the present invention is transfected into cells and then the level of miRNA-122 in the cells is quantified to confirm that the level of the miRNA-122 is lower than that in untreated cells. Alternatively, the evaluation can be performed, for example, by administering the oligonucleotide derivative according to the present invention in a mammal and quantifying the level of miRNA-122 in the liver to confirm that the miRNA-122 level is lower than before the administration thereof.

Next, a detailed description will be given of a conjugated oligonucleotide derivative according to the present invention.

The oligonucleotide derivative according to the present invention may be a conjugated oligonucleotide derivative having at least one ligand bound thereto. In the present specification, the term ligand means a substance that allows cell targeting, tissue targeting, functionality improvement, and the like by the oligonucleotide derivative according to the present invention.

In the conjugated oligonucleotide derivative, a ligand can be bound to the 5' end, the 3' end, or both the 5' end and the 3' end of an oligonucleotide derivative. The ligand can be bound to the oligonucleotide derivative by an usual method.

In the conjugated oligonucleotide derivative, a plurality of ligands may be bound to an oligonucleotide derivative. In this case, a conjugated oligonucleotide derivative having two to five ligands bound thereto is preferably used, and a conjugated oligonucleotide derivative having three ligands bound thereto is more preferably used. When three ligands are bound thereto, for example, the three ligands may be bound to the 5' end or the 3' end of the oligonucleotide derivative. Alternatively, for example, one of the three ligands may be bound to the 5' end thereof and two of the three ligands may be bound to the 3' end thereof. The number of ligands can be appropriately selected in a range allowing the present invention to be effective.

Examples of ligands usable in the conjugated oligonucleotide derivative according to the present invention include tocopherol, cholesterol, PSMA (prostate-specific membrane antigen), polyethylene glycol, vitamin A, folic acid, fatty chain, peptides, transferrins, aptamers, mannose, GalNAC (N-acetylgalactosamine), anisamide, other surface antigen-recognizing low molecular weight compounds or high molecular weight compounds, and combinations thereof. In a conjugated oligonucleotide derivative having a plurality of ligands bound thereto, the ligands bound thereto may be a plurality of ligands of the same kind or a combination of ligands of different kinds. Any ligand that allows the effects of the present invention to be obtained can be appropriately selected.

Examples of the conjugated oligonucleotide derivative according to the present invention include conjugated AMOs targeting miRNA-122 as below:
AMO122_SMe_PS_5'Toc (SEQ ID NO: 5): tocopherol is bound to the 5' end of AMO122_SMe_PS;
AMO122_SMe_PS_5'Chol (SEQ ID NO: 5): cholesterol is bound to the 5' end of AMO122_SMe_PS;
AMO122_SMe_PS_3'Chol (SEQ ID NO: 5): cholesterol is bound to the 3' end of AMO122_SMe_PS; and
AMO21_SMe_PS_5'PMSA (SEQ ID NO: 3): PMSA (prostate membrane antigen) is bound to the 5' end of AMO21_SMe_PS.

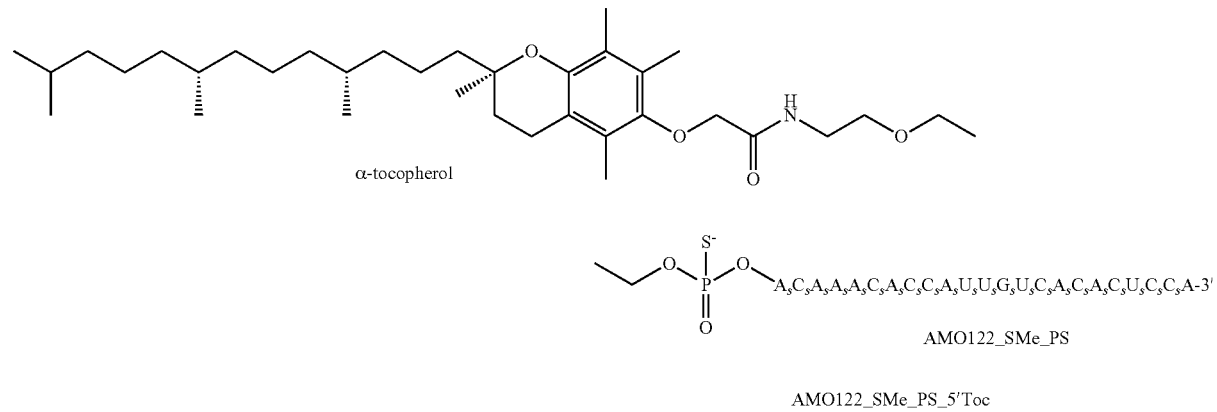

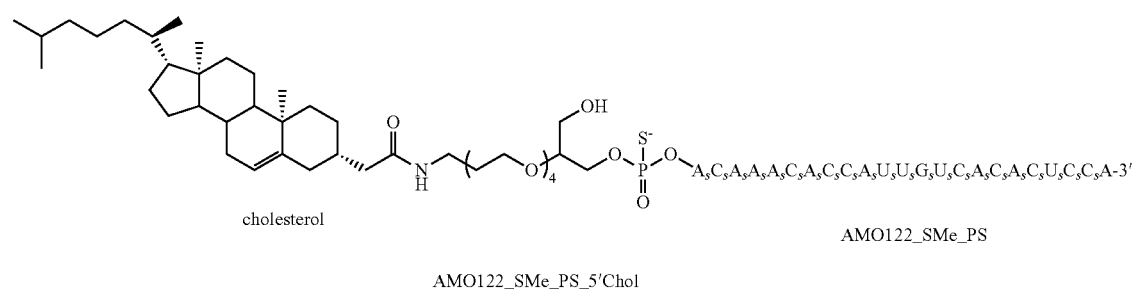

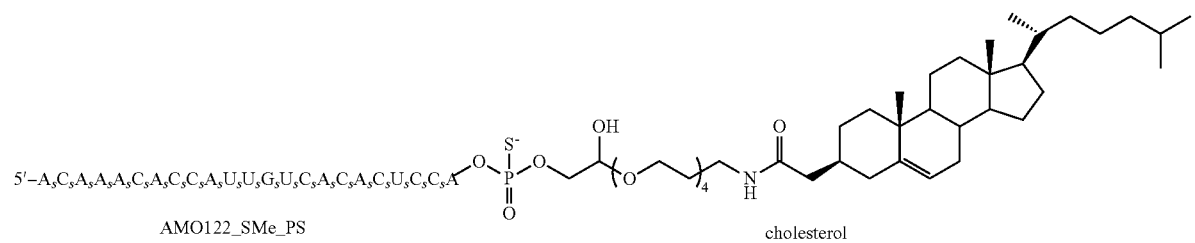

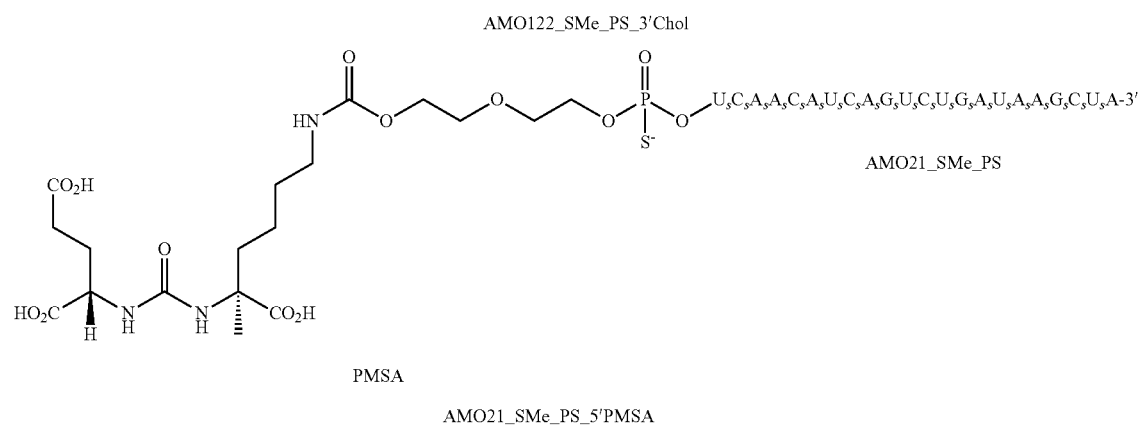

Conjugated oligonucleotide derivatives according to the present invention allow cell targeting, tissue targeting, functionality improvement, and the like by oligonucleotide derivative. For example, a conjugated oligonucleotide derivative using tocopherol as a ligand can achieve liver tissue targeting, and a conjugated oligonucleotide derivative using PSMA as a ligand can achieve prostate tissue targeting. For example, a conjugated oligonucleotide derivative using polyethylene glycol as a ligand improves retainability in blood. In addition, in a conjugated oligonucleotide derivative having a plurality of ligands bound thereto, for example, binding of a plurality of ligands that will bind to a certain kind of receptor can enhance interaction between the ligands and the receptor, further ensuring tissue targeting. Furthermore, for example, by using a conjugated oligonucleotide derivative having a combination of tocopherol and polyethylene glycol, as a ligand, bound thereto, tissue targeting and retainability in blood can be achieved simultaneously, thereby further ensuring liver tissue targeting.

Next, a description will be given of a method for synthesizing the oligonucleotide derivative according to the present invention.

The oligonucleotide derivative according to the present invention can be synthesized by an amidite method using a DNA synthesizer. For example, an AMO comprising SMe_PS (phosphorothioate) can be synthesized using a controlled pore glass (CPG) on which a 2'-OMe-4'-thio (in which a hydroxyl group at position 2' of a furanose ring of the sugar moiety of a nucleic acid has been methylated and an oxygen atom at position 4' of the furanose ring of the sugar moiety thereof has been substituted with a sulfur atom) ribonucleoside is supported and an amidite of 2'-OMe-4'-thio ribonucleoside, by sulfurization of phosphoric acid with 3H-1,2-benzodithiol-3-one-1,1-dioxide (Beaucage reagent). As an conjugated oligonucleotide derivative, for example, AMO122_SMe_PS_5'Toc can be synthesized in the same manner as above using an α-tocopherol amidite synthesized from α-tocopherol, and for example, AMO21_SMe_PS_5'PMSA can be synthesized in the same manner as above using an amidite of a 5'PMSA ligand synthesized from L-lysine. Various CPGs and amidites used in condensation reaction by the amidite method may be commercially available products. Any synthesis method that allows the effects of the present invention to be obtained can be appropriately selected.

(2. Pharmaceutical Composition for Treatment)

A pharmaceutical composition for treatment including the oligonucleotide derivative according to the present invention exhibits treatment effect, for example, through direct regulation of mRNA, regulation of miRNA function, or the like.

Regarding treatment effect through the regulation of miRNA function, for example, since miRNA-21 is up-regulated in various cancers such as liver cancer, pancreatic cancer, stomach cancer, breast cancer, and lung cancer as described above, administration of an miRNA-21-targeting AMO can inhibit the function of miRNA-21 in vivo and thus can exhibit treatment effects against the above cancers. In addition, for example, since miRNA-122 is involved in the replication of HCV as described above, administration of a miRNA-122-targeting AMO can inhibit the function of miRNA-122 and thus can exhibit a treatment effect against hepatitis C. Any disease against which the present invention can be effectively applied can be appropriately selected.

The oligonucleotide derivative according to the present invention has excellent effect persistence enough for in vivo use and thermal stability. Therefore, efficient regulation of miRNA function can be achieved and thus effective treatment effect is obtainable.

Administration of the pharmaceutical composition for treatment according the present invention to mammals can be performed, for example, through injection, oral administration, sublingual administration, and the like. Examples of injection administration include intravenous administration, intraarterial injection, intradermal injection, subcutaneous injection, intramuscular injection, and intraperitoneal injection. In addition, regarding dosage form, the pharmaceutical composition can be appropriately prepared into injection, sublingual tablet, granules, powder, or the like. For example, when the pharmaceutical composition is an injection, the composition can be prepared into an aqueous injection, a nonaqueous injection, a suspension injection, a solid injection, or the like, for an injection agent. When the composition is prepared into an injection agent, one or more additives may also be added, such as a solubilizer, a buffering agent, a tonicity agent, a stabilizer, a preservative, and/or a soothing agent. When prepared as an oral agent, an additives, a binder, a disintegrating agent, a thickener, and/or a dispersing agent, or the like that are commonly used can be appropriately included. The pharmaceutical composition for treatment may further appropriately include other active ingredients. Any administration method, any dosage form, any additive, and the like that allow the effects of the present invention to be obtained can be appropriately selected.

When the pharmaceutical composition for treatment according to the present invention is administered to a mammal, for example, administration may be carried out by dissolving the oligonucleotide derivative in a solvent commonly used for injection agents or dissolving the oligonucleotide derivative embedded in liposome in a solvent. Any administration method that allows the effects of the present invention to be obtained can be appropriately selected.

(3. Pharmaceutical Composition for Diagnosis)

A pharmaceutical composition for diagnosis including the oligonucleotide derivative according to the present invention exhibits treatment effect, for example, through the regulation of miRNA function.

For example, when carrying out in-vivo administration of an AMO targeting an miRNA as a biomarker of a specific cancer, a tracer detectable from outside the body is bound to the AMO in advance, with the result that binding of the AMO to the target miRNA enables the diagnosis of cancer by means of imaging (for example, PET). In addition, for example, by adding an AMO labelled with some label (such as a fluorescent label or a radioisotope label) into a tissue, blood, or the like collected from a living body, the confirmation of intracellular expression of the target miRNA and functional analysis thereof can be performed, as well as the quantification of the target miRNA in the tissue, the blood, or the like can also be performed. In addition to that, for example, by administering the AMO in vivo to inhibit the expression of the target miRNA, miRNA expression analysis can be made. Any diagnostic use for which the present invention is effective can be appropriately selected.

The AMO according to the present invention has excellent effect persistence enough for in vivo use and thermal stability and therefore can stably bind to a target miRNA in vivo and can inhibit the function of the target miRNA, thereby ensuring diagnosis using the AMO.

The administration method, the dosage form, additives, and the like for the pharmaceutical composition for diagnosis according to the present invention are the same as those described above.

(4. Oligonucleotide Derivative for Inhibiting miRNA Function)

An oligonucleotide derivative for inhibiting miRNA function according to the present invention comprises, similarly as described above, repeating structural units represented by the following general formula (1):

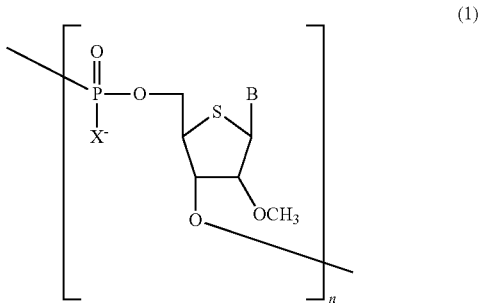

(wherein B represents adenine, guanine, cytosine, or uracil; X represents a sulfur atom or an oxygen atom; n represents an integer of 6 to 60; and B and X are independently represented in each of the repeating structural units), wherein X represents a sulfur atom in at least one of the repeating structural units represented by the general formula (1). In addition, in the oligonucleotide derivative for inhibiting miRNA function according to the present invention, similarly as described above, X may represent a sulfur atom in all of the repeating structural units represented by the general formula (1). Such an oligonucleotide derivative for inhibiting miRNA function comprising PS, namely, phosphorothioate has excellent effect persistence enough for in vivo use and thermal stability and therefore can be preferably used in the present invention.

The oligonucleotide derivative for inhibiting miRNA function according to the present invention may have, similarly to the above, at least one ligand bound to the 5' end, the 3' end, or both the 5' end and the 3' end. Such a conjugated oligonucleotide derivative for inhibiting miRNA function can achieve cell targeting, tissue targeting, functionality improvement, and the like by oligonucleotide derivative.

The oligonucleotide derivative for inhibiting miRNA function according to the present invention can inhibit miRNA function in vivo or in vitro. The oligonucleotide derivative for inhibiting miRNA function according to the present invention can target various miRNAs, similarly to the above.

Evaluation of the inhibition of miRNA function by the oligonucleotide derivative for inhibiting miRNA function according to the present invention can be performed as follows. In the same way as above, for example, when miRNA-122 is targeted, an oligonucleotide derivative for inhibiting miRNA-122 function according to the present invention is transfected into cells, then, the level of miRNA-122 in the cells is quantified to confirm that the level of miRNA-122 is less than that in the untreated cells. In addition, for example, the evaluation can be performed by administering the oligonucleotide derivative for inhibiting miRNA-122 function according to the present invention to a mammal and quantifying the level of miRNA-122 in the liver to confirm that the level of miRNA-122 after the administration is lower than before the administration.

The oligonucleotide derivative for inhibiting miRNA function according to the present invention may comprise, similarly to the above, a sequence complementary to the entire sequence or a partial sequence of miRNA. In this case, the derivative can be used as a miRNA-targeting AMO. When the oligonucleotide derivative for inhibiting miRNA function according to the present invention is administered, for example, in vivo, the oligonucleotide derivative forms double strands together with the miRNA in vivo, thereby inhibiting miRNA function. Additionally, the miRNA in this case may be, similarly to the above, miRNA-21 or miRNA-122.

The present invention is not limited to the embodiments described above and various modifications and applications can be made.

Example 1

Hereinbelow, a detailed description will be given of the present invention with reference to Examples. However, the present invention is not limited to the Examples. In addition, "%" represents % by mass unless otherwise specified.

(Synthesis of AMOs)

Each AMO was synthesized in the following manner. The name and SEQ ID NO of each AMO are indicated below. In the following Examples, an AMO that is fully complementary to miRNA-21 is referred to as AMO 21, and an AMO that is fully complementary to miRNA-122 is referred to as AMO 122.

1. Unconjugated AMOs 21

AMO21(32)_SMe (SEQ ID NO: 4)
AMO21_SMe_PO (SEQ ID NO: 3)
AMO21_SMe_PS (SEQ ID NO: 3)

2. Unconjugated AMOs 122

AMO122_SMe_PO (SEQ ID NO: 5)
AMO122_SMe_PS (SEQ ID NO: 5)

3. Conjugated AMOs 122

AMO122_SMe_PS_5'Toc (SEQ ID NO: 5)
AMO122_SMe_PS_5'Chol (SEQ ID NO: 5)
AMO122_SMe_PS_3'Chol (SEQ ID NO: 5)

4. Conjugated AMOs 21

AMO21_SMe_PS_5'PMSA (SEQ ID NO: 3)

5. Comparative Examples

Unconjugated AMOs 21

AMO21(32)_Me (SEQ ID NO: 4)
AMO21_Me_PO (SEQ ID NO: 3)
AMO21_FMe_PO (a methoxy group in the 2' position of AMO21_Me_PO is substituted with fluorine) (SEQ ID NO: 3)
AMO21_SFMe_PO (a methoxy group in the 2' position of AMO21_SMe_PO is substituted with fluorine) (SEQ ID NO: 3)

6. Comparative Examples

Unconjugated AMOs 122

AMO122_Me_PO (SEQ ID NO: 5)
AMO122_Me_PS (SEQ ID NO: 5)

7. Comparative Examples

Conjugated AMOs 122

AMO122_Me_PS_5'Toc (SEQ ID NO: 5)
AMO122_Me_PS_5'Chol (SEQ ID NO: 5)
AMO122_Me_PS_3'Chol (SEQ ID NO: 5)

8. Comparative Example

Conjugated AMO 21

AMO21_Me_PS_5'PMSA (SEQ ID NO: 3)

The following formulas represent repeating structural units of the unconjugated AMOs 21:

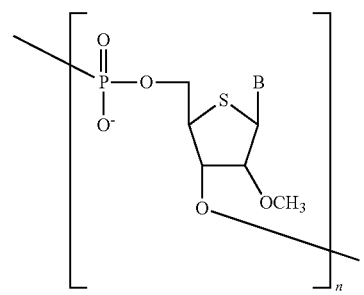

AMO21(32)_SMe

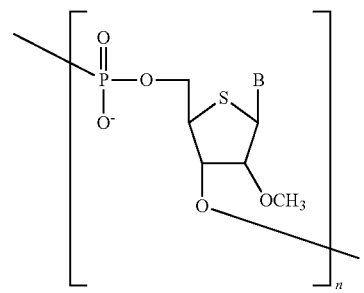

AMO21_SMe_PO

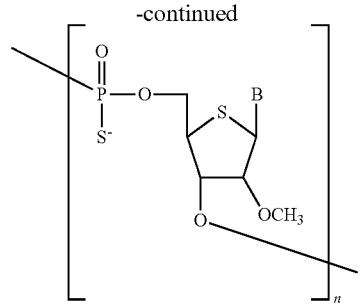

AMO21_SMe_PS

The following formulas represent repeating structural units of the unconjugated AMOs 122:

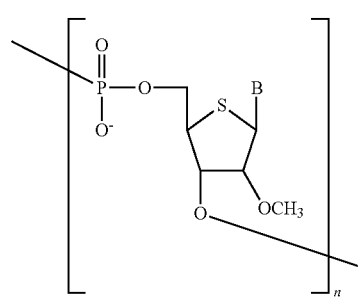

AMO122_SMe_PO

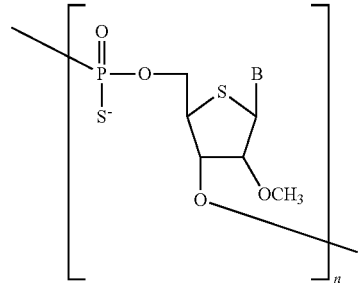

AMO122_SMe_PS

The following formulas represent structures and repeating structural units of the conjugated AMOs 122 and the conjugated AMO 21.

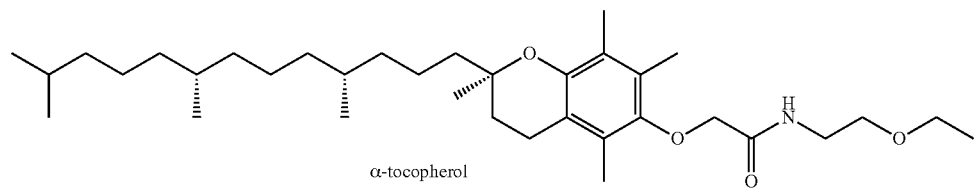

α-tocopherol

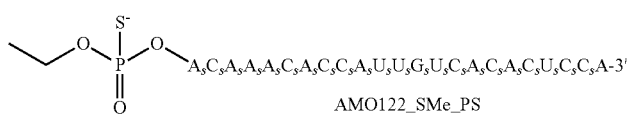

AMO122_SMe_PS

AMO122_SMe_PS_5'Toc

-continued
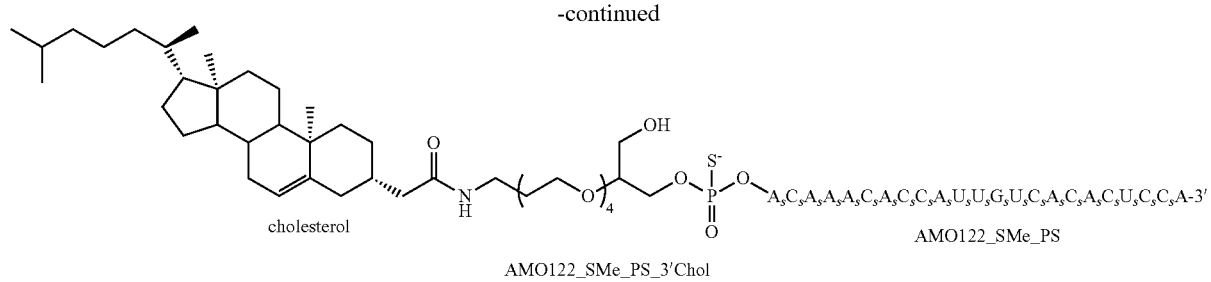
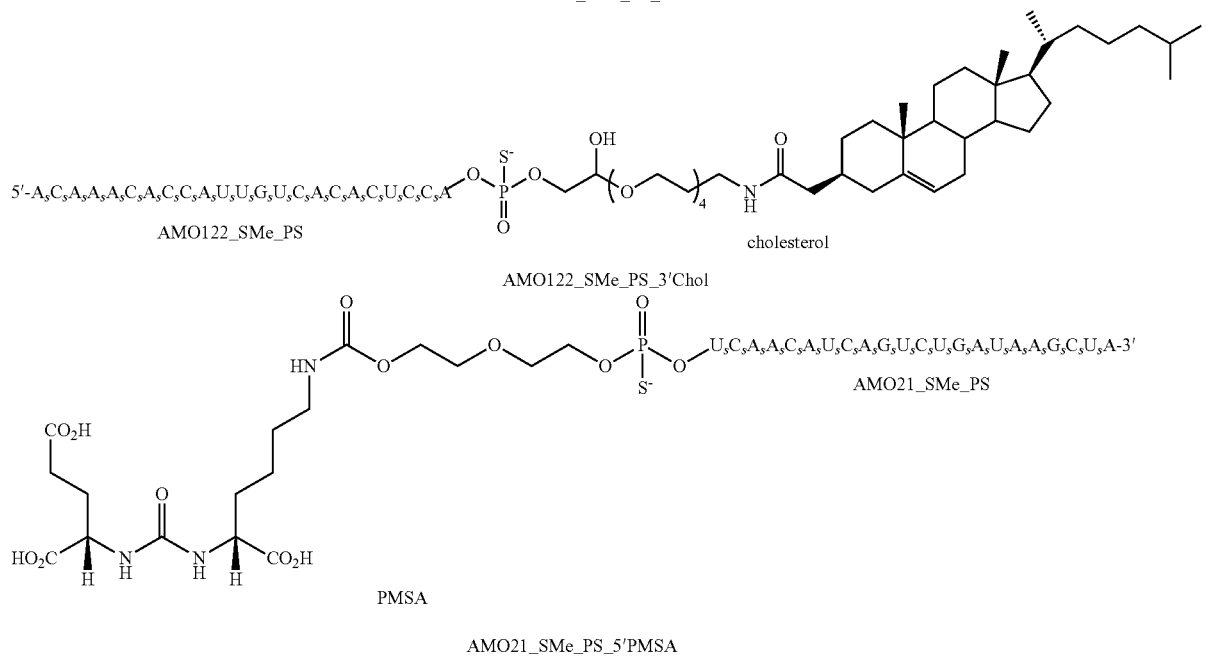
The following formulas represent repeating structural units of the unconjugated AMOs 21 used in the Comparative Examples:
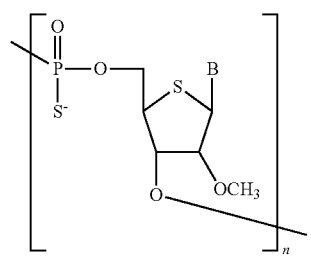
-continued
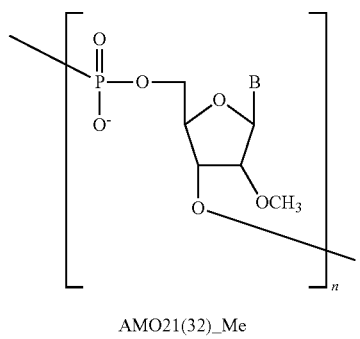
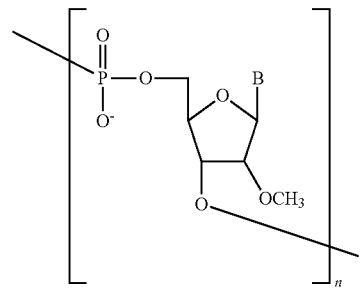

21
-continued
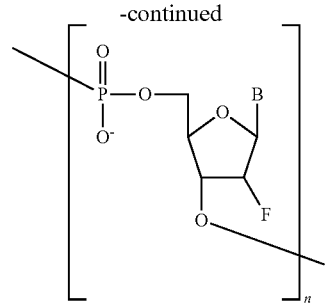
AMO21_FMe_PO
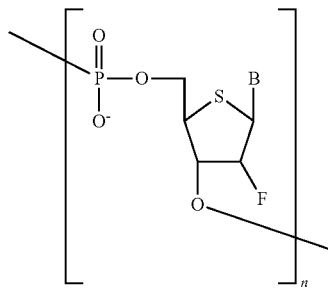
AMO21_SFMe_PO
The following formulas represent repeating structural units of the unconjugated AMO122 used in the Comparative Examples:
22
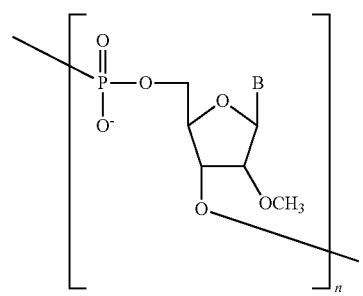
AMO122_Me_PO
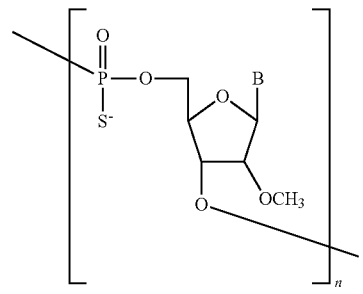
AMO122_Me_PS
The following formulas represent structures and repeating structural units of the conjugated AMO122 and the conjugated AMO21 used in the Comparative Examples:
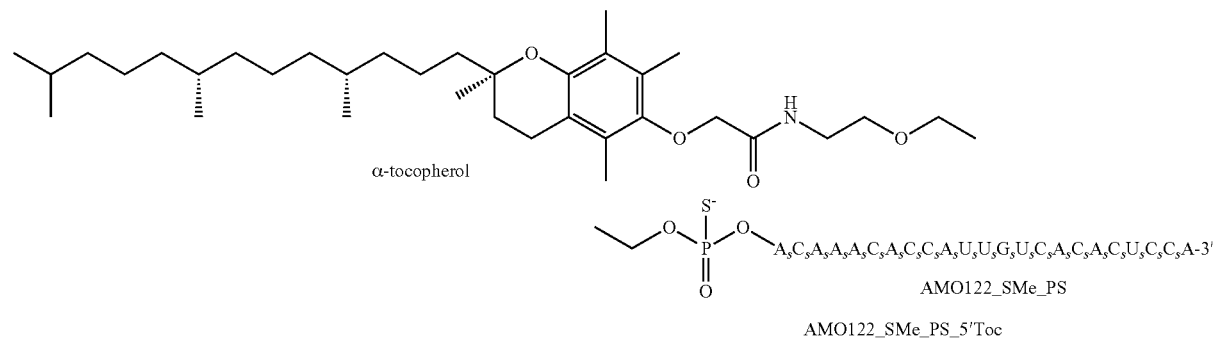
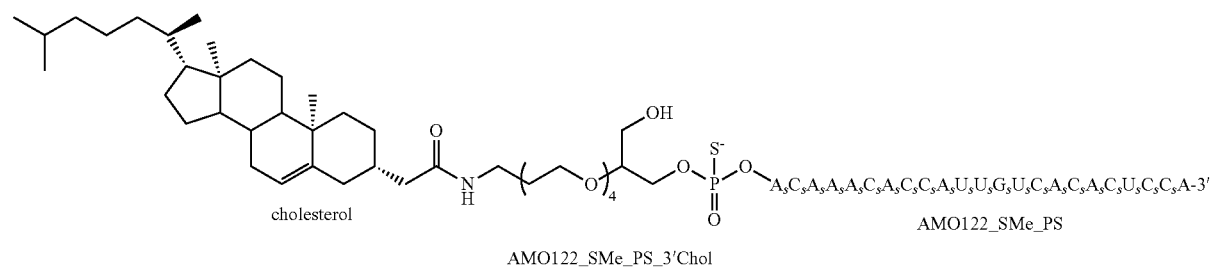
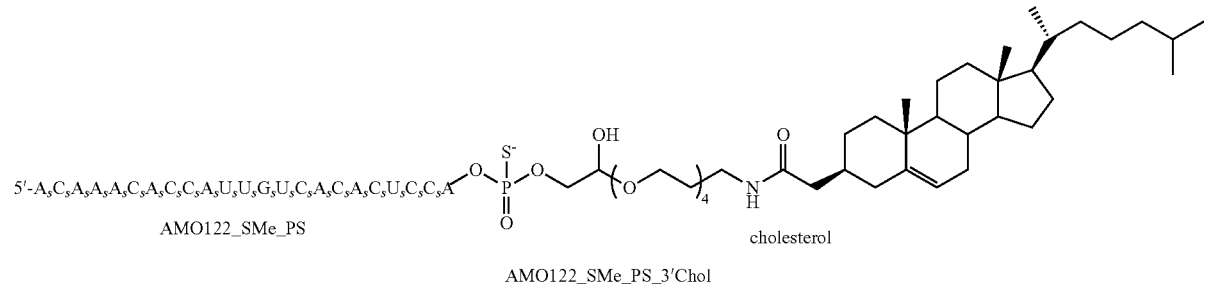

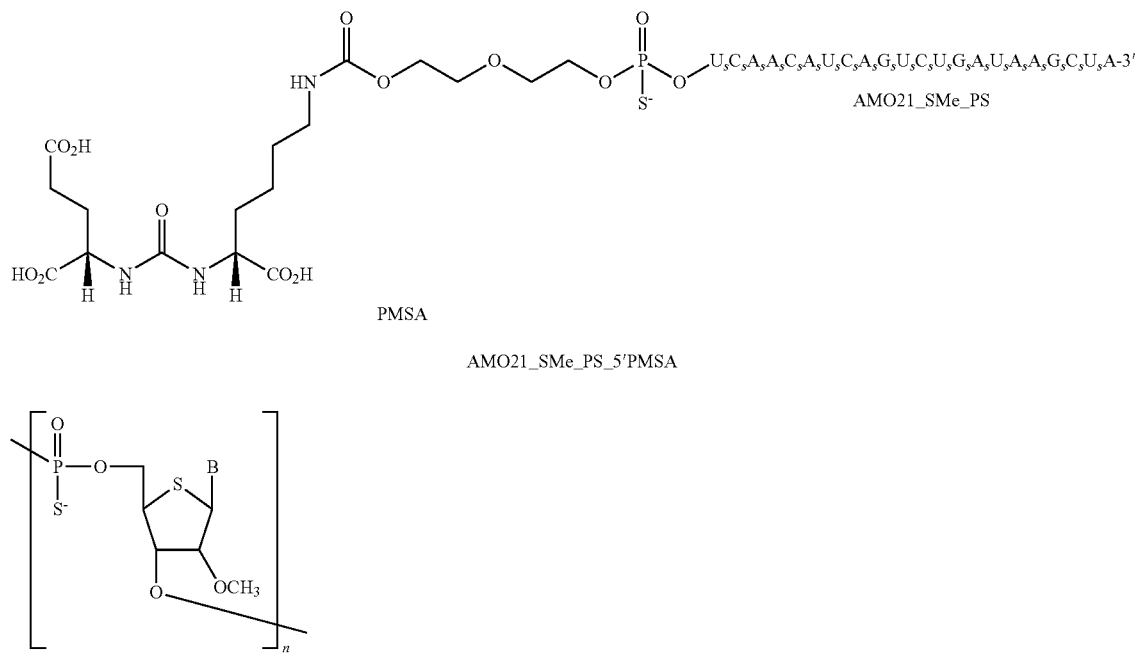

AMO21_SMe_PS_5'PMSA (A. Methods for Synthesizing AMO Comprising Me_PO and AMO Comprising SMe_PO)

The AMOs were synthesized using a DNA synthesizer: ABI 3400 (manufactured by Applied Biosystem Co., Ltd.) in accordance with a usual DNA solid phase synthesis method.

Condensation reaction of the AMO comprising Me_PO was performed using a CPG on which 1 μmol of 2'-OMe (a hydroxyl group at position 2' of a furanose ring of the sugar moiety of a nucleic acid has been methylated) nucleoside is supported (manufactured by Glen Research Co., Ltd.) and a 2'-OMe nucleoside amidite (manufactured by Glen Research Co., Ltd). The 2'-OMe nucleoside amidite was prepared in a 0.1 M acetonitrile solution to be used for condensation reaction.

Condensation reaction of the AMO comprising SMe_PO was performed using a CPG on which 1 μmol of 2'-OMe-4'-thio (a hydroxyl group at position 2' of a furanose ring of the sugar moiety of a nucleic acid has been methylated and an oxygen atom at position 4' of the sugar moiety furanose ring has been substituted with a sulfur atom) ribonucleoside is supported and a 2'-OMe-4'-thio ribonucleoside amidite. The CPG with the 2'-OMe-4'-thio ribonucleoside supported thereon and the 2'-OMe-4'-thio ribonucleoside amidite, respectively, were synthesized from the CPG with the 2'-OMe nucleoside supported thereon and the 2'-OMe nucleoside amidite, respectively, in accordance with a usual method. The 2'-OMe-4'-thio ribonucleoside amidite was prepared in a 0.1 M acetonitrile solution to be used for condensation reaction.

By adding 3% TCA (trichloroacetic acid), a DMTr group in the CPG with the 2'-OMe nucleoside supported thereon or the CPG with the 2'-OMe-4'-thio ribonucleoside supported thereon was removed, and then, 1H-tetrazole was used as an activator to perform the condensation of the CPGs, respectively, with the 2'-OMe nucleoside amidite or the 2'-OMe-4'-thio ribonucleoside amidite, respectively. Condensation time was 600 seconds. Next, after capping by reacting acetic anhydride with unreacted hydroxyl group, oxidation of phosphoric acid was performed using iodine as an oxidizer in the presence of water. This cycle was repeated to synthesize an AMO supported on the solid phase (CPG). The following represents a synthesis scheme for the AMO comprising SMe_PO.

Synthesis Scheme for AMO Comprising SMe_PO

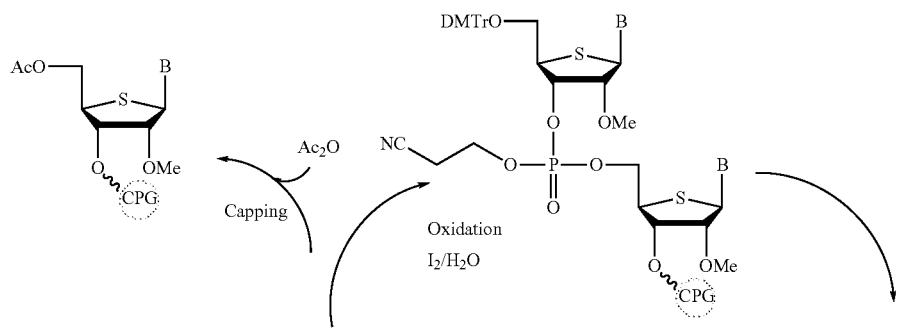

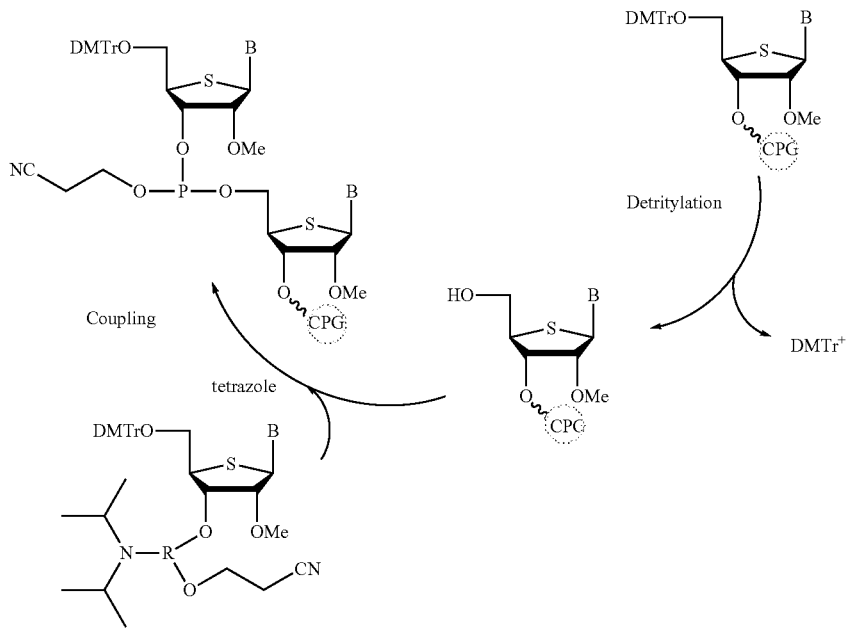

(B. Methods for Synthesizing AMO Comprising Me_PS and AMO comprising SMe_PS)

Instead of iodine as the oxidizer in section A above, 3H1,2-benzodithiol-3-one-1,1-dioxide (Beaucage reagent) was used for the sulfurization of phosphoric acid to synthesize AMOs in the same manner as section A above. The following is a synthesis scheme for the AMO comprising SMe_PS.

Synthesis Scheme for AMO Comprising SMe_PS

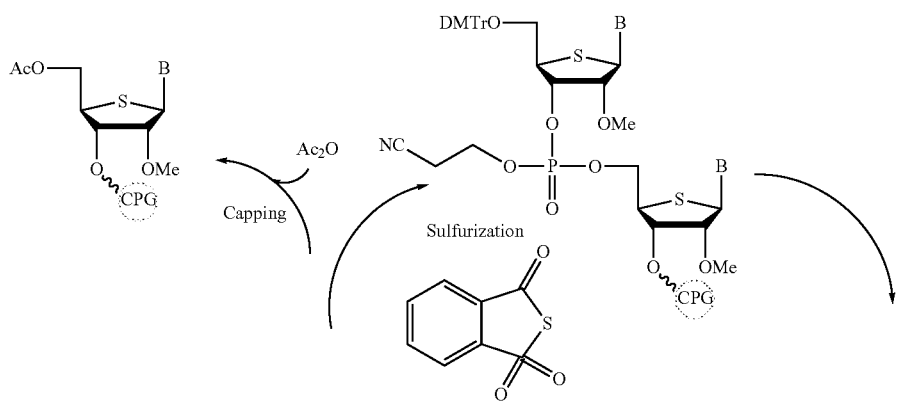

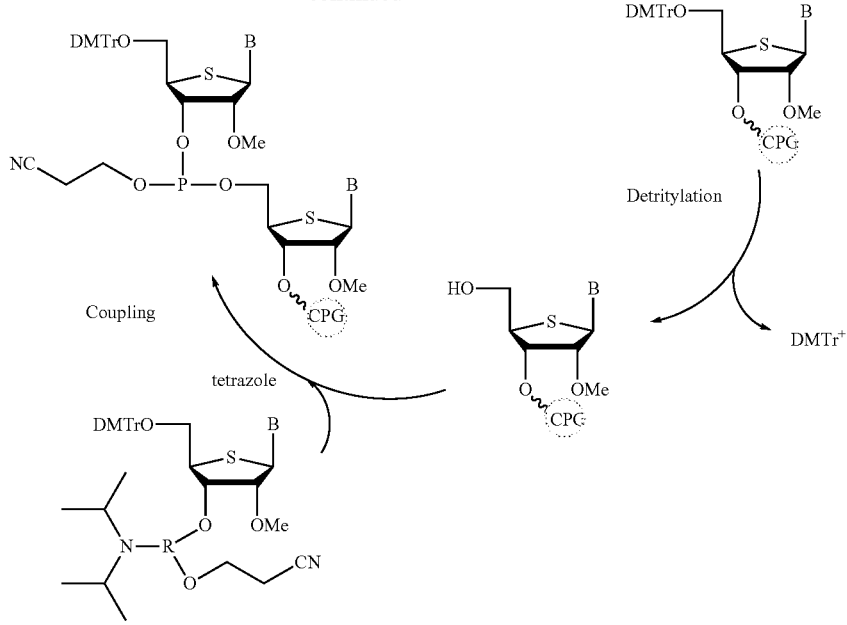
(C. Method for Synthesizing Conjugated AMO)
An α-tocopherol amidite was prepared in 0.1 M of a 10% THF/acetonitrile solution and, condensation reactions were performed in the same manner as section B above to obtain AMO122_Me_PS_5'Toc and AMO122_SMe_PS_5'Toc. The α-tocopherol amidite was synthesized from α-tocopherol as below:
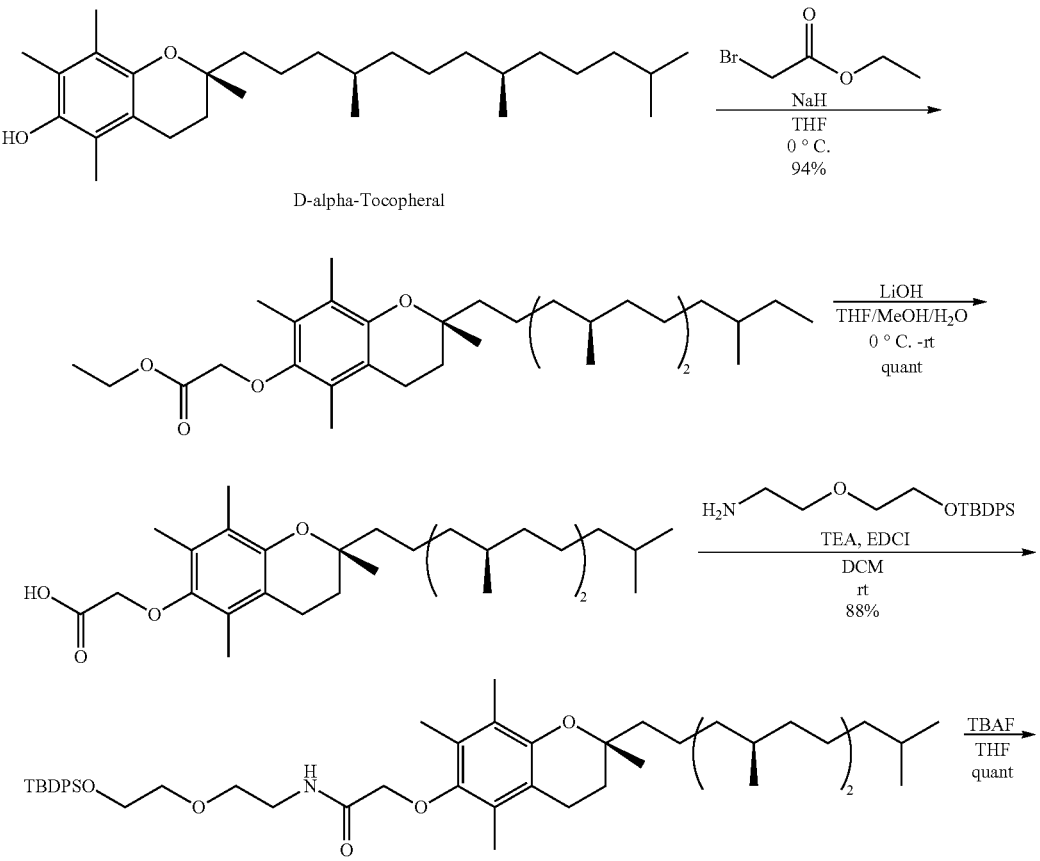

-continued

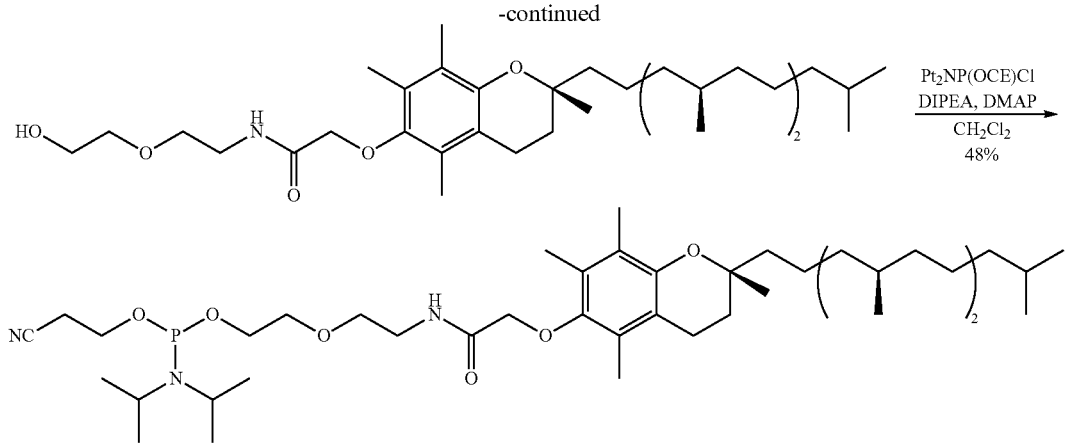

A 5'-Cholesteryl-TEG (triethylene glycol) amidite (manufactured by Glen Research Co., Ltd.) was prepared in 0.1 M of a 10% THF/acetonitrile solution, and condensation reactions were performed in the same manner as section B above to obtain AMO122_Me_PS_5'Chol and AMO122_SMe_PS_5'Chol.

Using a CPG resin with 1 μmol of 3'-Cholesteryl-TEG supported thereon (manufactured by Glen Research Co. Ltd.), condensation reactions were performed in the same manner as section B above to obtain AMO122_Me_PS_3'Chol and AMO122_SMe_PS_3'Chol.

A 5'-PMSA ligand amidite was prepared in 0.1 M of acetonitrile solution, and condensation reactions were performed in the same manner as section B above to obtain AMO21_Me_PS_5'PMSA and AMO21 SMe_PS_5'PMSA. The 5'-PMSA ligand amidite was synthesized from L-lysine as below:

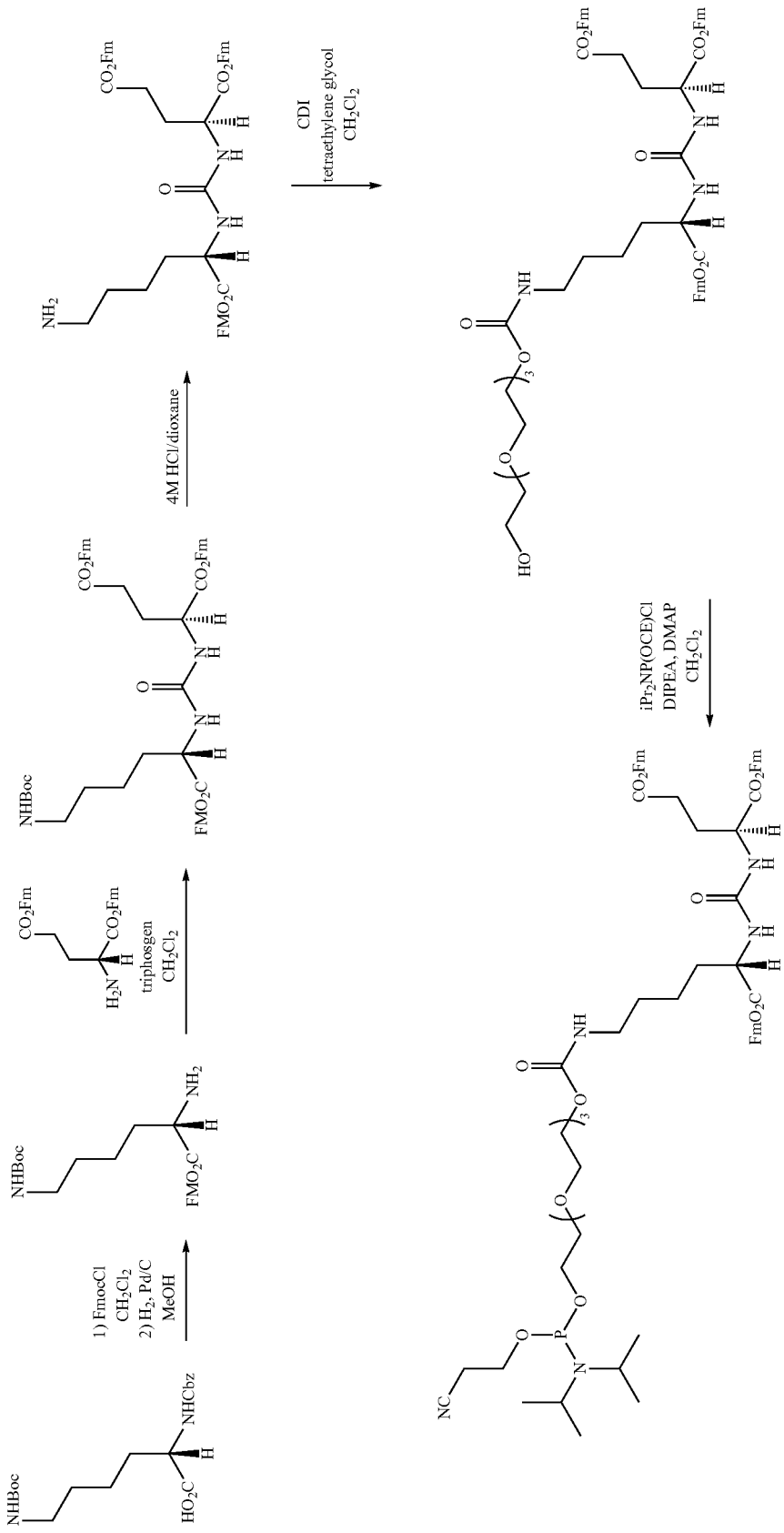

(D. Methods for Synthesizing AMO21_FMe_PO and AMO21_SFMe_PO)

The Comparative Examples AMO21_FMe_PO and AMO21_SFMe_PO were synthesized in the same manner as section A above in accordance with the usual method.

After completion of the syntheses, each CPG with each AMO supported thereon was transferred into a vial. Then, 28% ammonia water/ethanol (3:1, 2 mL) was added and each vial was allowed to stand at 55° C. for 16 hours to perform cleavage and deprotection of the each AMO. The reaction solution was filtered with a glass filter and the solvent was distilled away under reduced pressure. The each unconjugated AMO synthesized in the state of having a DMTr group left at the 5' end thereof was roughly purified by C18 reverse phase HPLC (J' sphere YMC ODS-M80, 150×4.6 mm, 5 to 50% acetonitrile in 0.1 N TEAA buffer, pH 7.0) to collect a fraction containing a full-length AMO having the DMTr group, and then the solvent was distilled away under reduced pressure. After performing desalination of the residue using Sep-Pak C18 (Waters), hydrochloric acid (pH 2.0) was added and treated at room temperature for 20 minutes to remove the DMTr group left at the 5' end. The obtained reaction solution was neutralized with diluted ammonia aqueous solution and then the solvent was distilled away under reduced pressure. The residue containing each of the conjugated and the unconjugated full-length AMOs was purified by C18 reverse phase HPLC (J' sphere YMC ODS-M80, 150×4.6 mm, 5 to 50% acetonitrile in 0.1 N TEAA buffer, pH 7.0), and then, desalination was performed using Sep-Pak C18 to obtain each AMO with high purity.

The structure of each AMO purified was analyzed by MALDI-TOF/MASS spectrometry (ULTRAFLEX TOF/TOF, manufactured by Bruker Daltonics) to obtain a molecular weight thereof. The analysis results are listed below:

AMO21_Me_PO: calculated mass, $C_{231}H_{302}N_{82}O_{150}P_{21}$ 7276.3 (M-H); observed mass, 7273.80.

AMO21_SMe_PO: calculated mass, $C_{231}H_{302}N_{82}O_{128}P_{21}S_{22}$ 7627.80 (M-H); observed mass, 7626.50.

AMO122_Me_PO: calculated mass, $C_{240}H_{318}N_{85}O_{154}P_{22}$ 7539.40 (M-H); observed mass, 7538.52.

AMO122_Me_PS: calculated mass, $C_{240}H_{318}N_{85}O_{132}P_{22}S_{22}$ 7891.89 (M-H); observed mass, 7886.64.

AMO122_SMe_PO: calculated mass, $C_{240}H_{318}N_{85}O_{131}P_{22}S_{23}$ 7906.87 (M-H); observed mass, 7906.72.

AMO122_SMe_PS: calculated mass, $C_{240}H_{318}N_{85}O_{109}P_{22}S_{45}$ 8261.36 (M-H); observed mass, 8261.66.

AMO122_Me_PS_5'Toc: calculated mass, $C_{275}H_{378}N_{86}O_{138}P_{23}S_{23}$ 8543.28 (M-H); observed mass, 4546.78.

AMO122_SMe_PS_5'Toc: calculated mass, $C_{275}H_{378}N_{86}O_{115}P_{23}S_{46}$ 8913.75 (M-H); observed mass, 8916.81.

AMO122_Me_PS_5'Chol: calculated mass, $C_{281}H_{390}N_{86}O_{140}P_{23}S_{23}$ 8661.36 (M-H); observed mass, 8662.17.

AMO122_SMe_PS_5'Chol: calculated mass, $C_{281}H_{390}N_{86}O_{112}P_{23}S_{46}$ 9030.83 (M-H); observed mass, 9033.77.

AMO122_Me_PS_3'Chol: calculated mass, $C_{281}H3_{90}N_{86}O_{140}P_{23}S_{23}$ 8661.36 (M-H); observed mass, 8662.04.

AMO122_SMe_PS_3'Chol: calculated mass, $C_{281}H_{390}N_{86}O_{112}P_{23}S_{46}$ 9030.83 (M-H); observed mass, 9032.13.

AMO122_Me_PS_5'PSMA: calculated mass, $C_{252}H_{338}N_{85}O_{143}P_{22}S_{22}$ 8231.99 (M-H); observed mass, 8231.99.

AMO122_SMe_PS_5'PSMA: calculated mass, $C_{252}H_{338}N_{85}O_{121}P_{22}S_{44}$ 8585.49 (M-H); observed mass, 8585.49.

FIG. 1 indicates sequences and 50% melting temperatures (Tm values) of the unconjugated AMO21 (22-mer series: SEQ ID NO: 3; 32-mer series: SEQ ID NO: 4). The results of measurement of the Tm values (measurement conditions: 10 mM of phosphate buffer (pH 7.0), 0.1 mM of EDTA, 1 mM of sodium chloride, 3 μM of strand concentration) showed that the unconjugated AMOs 21 according to the Example of the present invention has an ability to form thermally stable double strands together with miRNA-21 as complementary chain RNA.

FIG. 2 indicates sequences and Tm values of the unconjugated AMO122 (SEQ ID NO: 5). The results of measurement of the Tm values (measurement conditions were the same as those described above) showed that the unconjugated AMOs 122 according to the Example of the present invention have an ability to form thermally stable double strands together with miRNA-122 as complementary chain RNA.

Example 2

Construction of miRNA Reporter Vector

A sequence formed by arranging two fully complementary sequences of miRNA-21 (SEQ ID NO: 6) or two fully complementary sequences of miRNA-122 (SEQ ID NO: 7) in series was cloned in a 3' untranslated region (3'-UTR) of a firefly luciferase gene in a pmirGLO vector (purchased from Promega K.K) to construct an miRNA reporter vector (FIG. 3). The pmirGLO vector expresses firefly luciferase (Fluc) and Renilla luciferase (Rluc).

Example 3

Assay of AMOs

Figure 4:
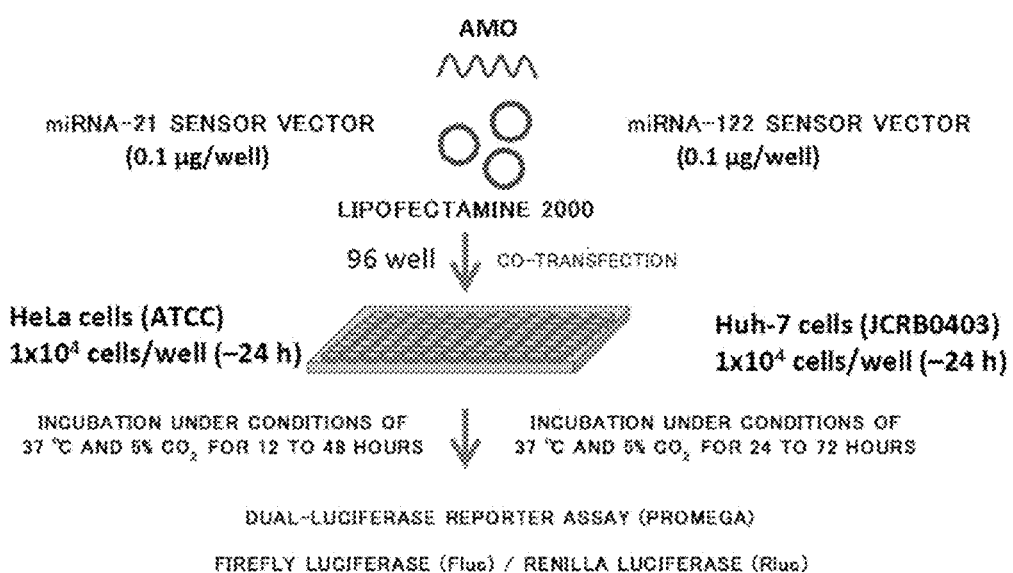
FIG. 4 is a view illustrating a protocol for evaluating the inhibitory effect of each AMO on miRNA.

As indicated in FIG. 4, HeLa cells (human cervical cancer cells) for miRNA-21 or Huh-7 cells (cells highly expressing miRNA-122) for miRNA-122 were seeded at a density of 10,000 cells in each well of a 96-well plate (a LumiNunc 96-well microplate) and then incubated at 37° C. in 5% $CO_2$ in air. Twenty-four hours later, each AMO and the above-mentioned reporter vector (0.1 μg/well) were co-transfected using LIPOFECTAMINE 2000 (purchased from Invitrogen, Inc.) and incubated. At that time, Opti-MEM (purchased from Invitrogen, Inc) was used as culture medium. Six hours later, the medium was replaced by a complete medium (a DMEM containing 10% FBS and an antibiotic) and again, incubation was performed. After 24 hours, 48 hours, and 72 hours from the co-transfection, the cells were dissolved in Lysis buffer to measure luciferase activity using a dual-luciferase reporter assay system (purchased from Promega K.K). Fluc/Rluc relative ratio (%) (FIGS. 5 to 12) represents relative values of activities of the individual AMO-administered cells when firefly luciferase activity value is normalized by Renilla luciferase activity and mirGLO-administered cell activity is set as 100%. The relative values were obtained by performing individual experiments at least three times to calculate average values and standard deviations thereof.

(Evaluation of Activities of Unconjugated AMOs 21)

Figure 5:
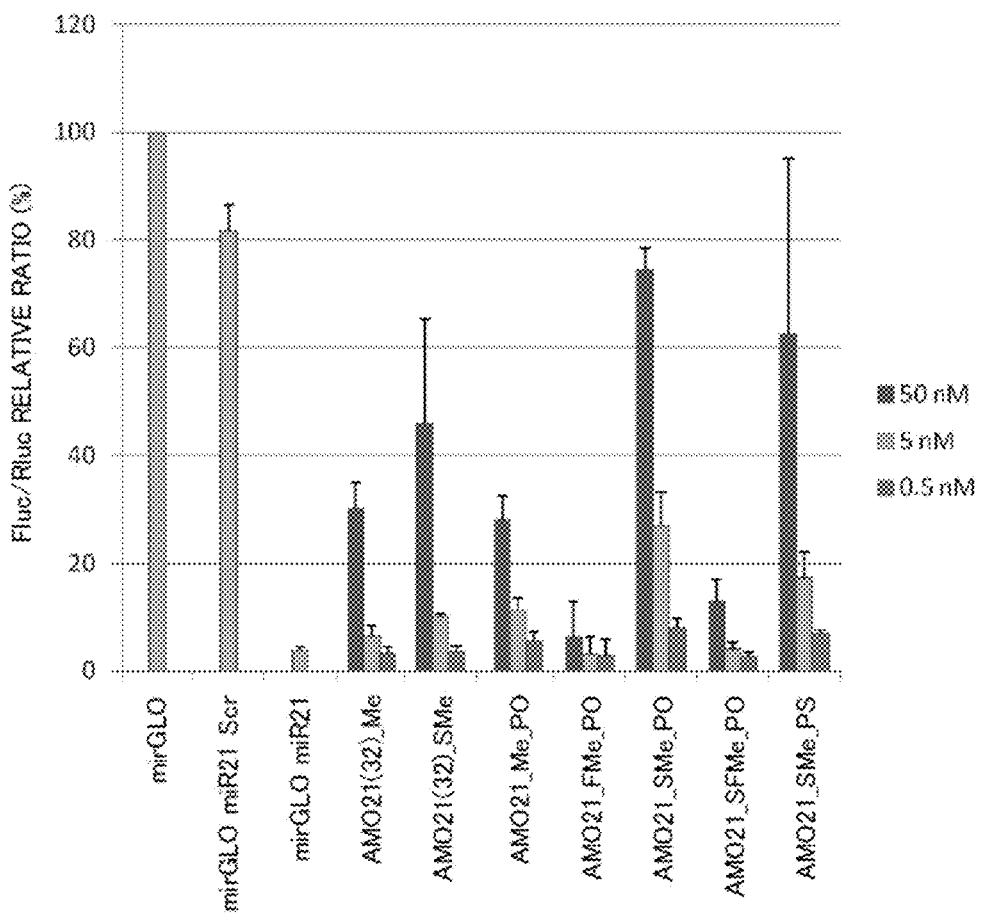
FIG. 5 is a graph depicting inhibitory effects of unconjugated AMOs 21 on miRNA-21.

FIG. 5 indicates results obtained after 24 hours from the co-transfection. The mirGLO represents a control in which only a reporter vector was added. The mirGLO miR21Scr (scramble) represents a control in which only a reporter vector having a different 3'-UTR sequence was added. Since miRNA-21 cannot bind to the 3'-UTR, the Fluc/Rluc relative ratio becomes high. The mirGLO miR21 represents a control in which the reporter vector and miRNA-21 were added. Since miRNA-21 binds to the 3'-UTR, the Fluc/Rluc relative ratio becomes low. In addition, in FIG. 5, the concentrations of the individual AMOs are 50 nM, 5 nM, and 0.5 nM in order from the left of the three columns of the individual AMOs.

As compared to the Comparative Examples AMO21(32)_Me, AMO21_Me_PO, AMO21_FMe_PO, and AMO21_SFMe_PO, the Fluc/Rluc relative ratio was shown to be dose-dependently higher in AMO21(32)_SMe, AMO21_SMePO, and AMO21_SMe_PS. This is due to the fact that, by binding of the unconjugated AMOs 21 according to the Example of the present invention to miRNA-21, miRNA-21 was not able to bind to the 3'-UTR of the reporter vector and therefore the Fluc/Rluc relative ratio became high. The results showed that the AMOs 21 according to the Example of the present invention inhibit miRNA-21.

(Evaluation of Activities of Unconjugated AMOs 122)

Figure 6:
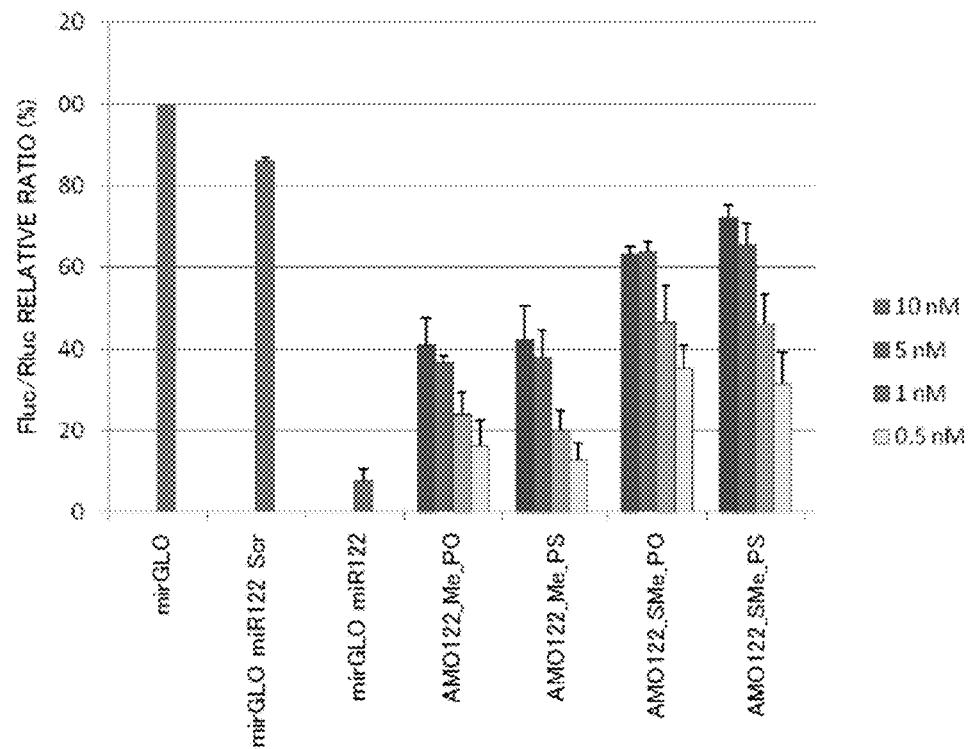
FIG. 6 is a graph depicting inhibitory effects of unconjugated AMOs 122 on miRNA-122 (after 24 hours from co-transfection)
Figure 7:
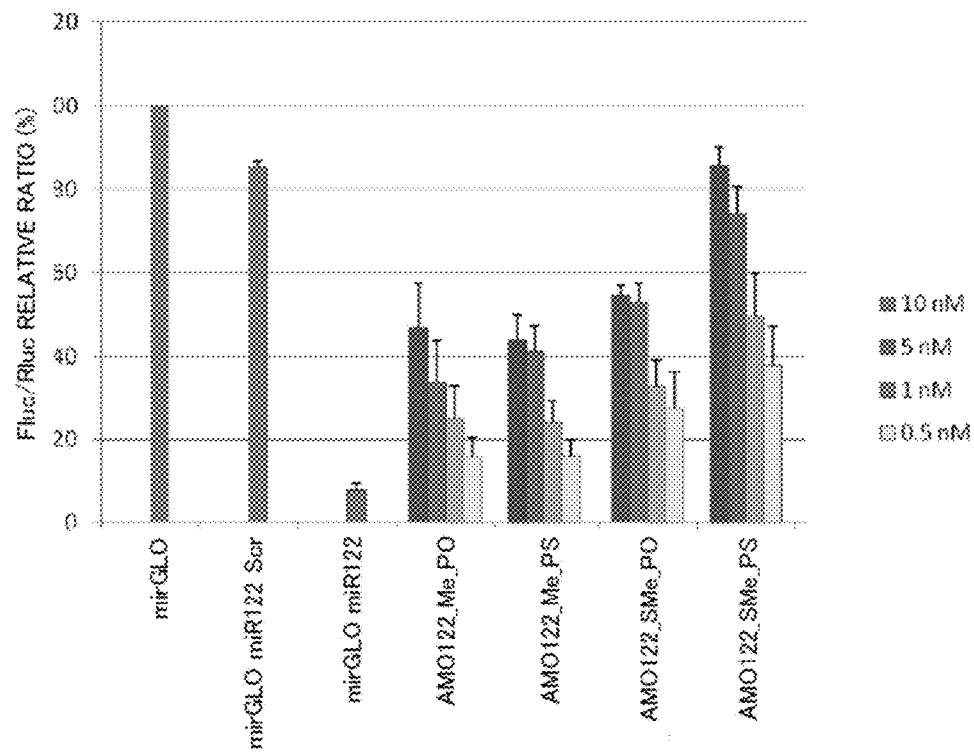
FIG. 7 is a graph depicting inhibitory effects of the unconjugated AMOs 122 on miRNA-122 (after 48 hours from co-transfection)
Figure 8:
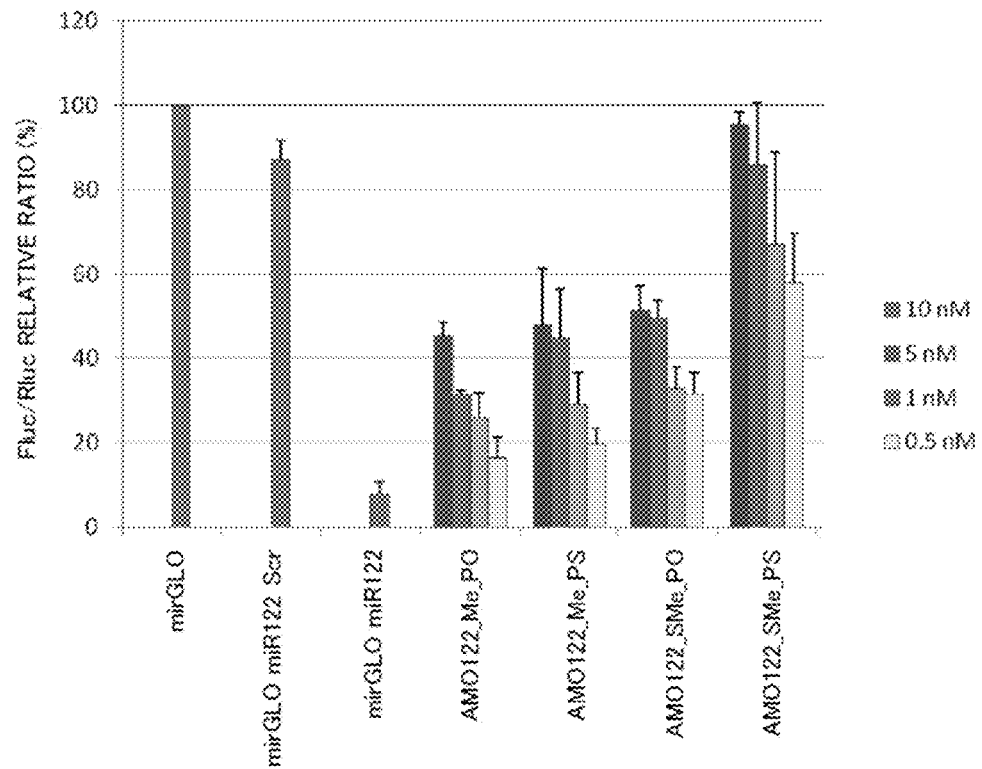
FIG. 8 is a graph depicting inhibitory effects of the unconjugated AMOs 122 on miRNA-122 (after 72 hours from co-transfection)

FIG. 6 indicates results after 24 hours from the co-transfection, FIG. 7 indicates results after 48 hours therefrom, and FIG. 8 indicates results after 72 hours therefrom. In FIGS. 6 to 8, the concentrations of the individual AMOs are 10 nM, 5 nM, 1 nM, and 0.5 nM in order from the left of the four columns of the individual AMOs.

In FIGS. 6 to 8, as compared to the Comparative Examples: AMO122_Me_PO and AMO122_Me_PS, the Fluc/Rluc relative ratio was shown to be dose-dependently higher in AMO122_SMe_PO and AMO122_SMe_PS.

Figure 9:
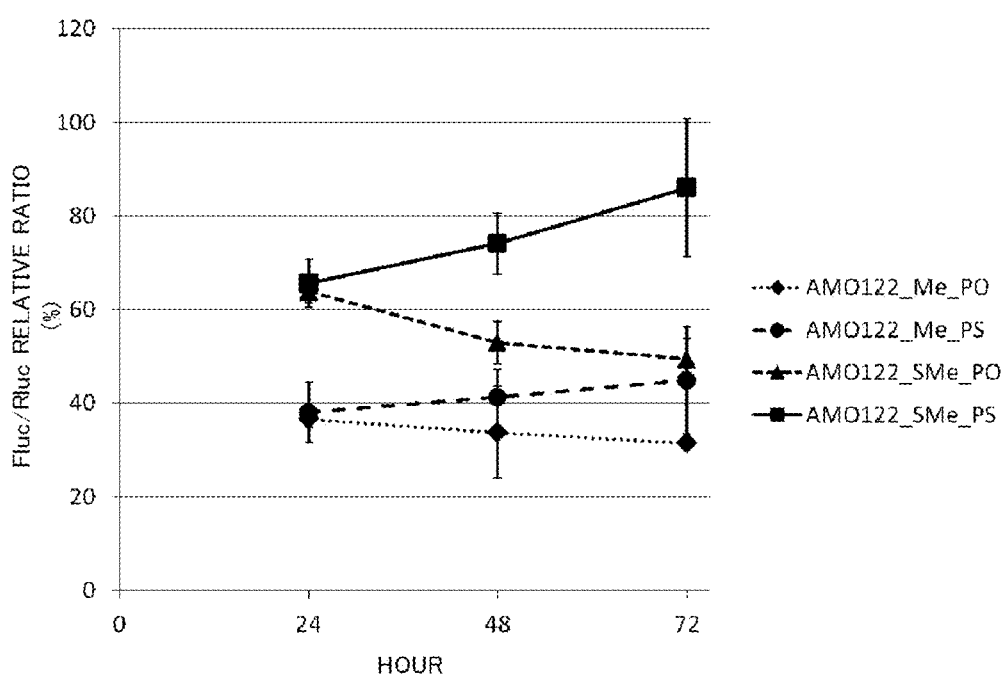
FIG. 9 is a graph depicting temporal changes in the inhibitory effects of the unconjugated AMOs 122 on miRNA-122.

Additionally, FIG. 9 indicates changes with the passage of time in the activities of the unconjugated AMOs 122 at an AMO concentration of 5 nM. As compared to the Comparative Examples AMO122_Me_PO and AMO122_Me_PS, AMO122 activity was favorably maintained in AMO122_SMe_PO and AMO122_SMe_PS and the AMO122 activity of the AMO122_SMe_PS improved with the passage of time. The results showed that the AMOs 122 according to the Example of the present invention consistently inhibit miRNA-122.

(Evaluation of Activities of Conjugated AMOs 122)

Figure 10:
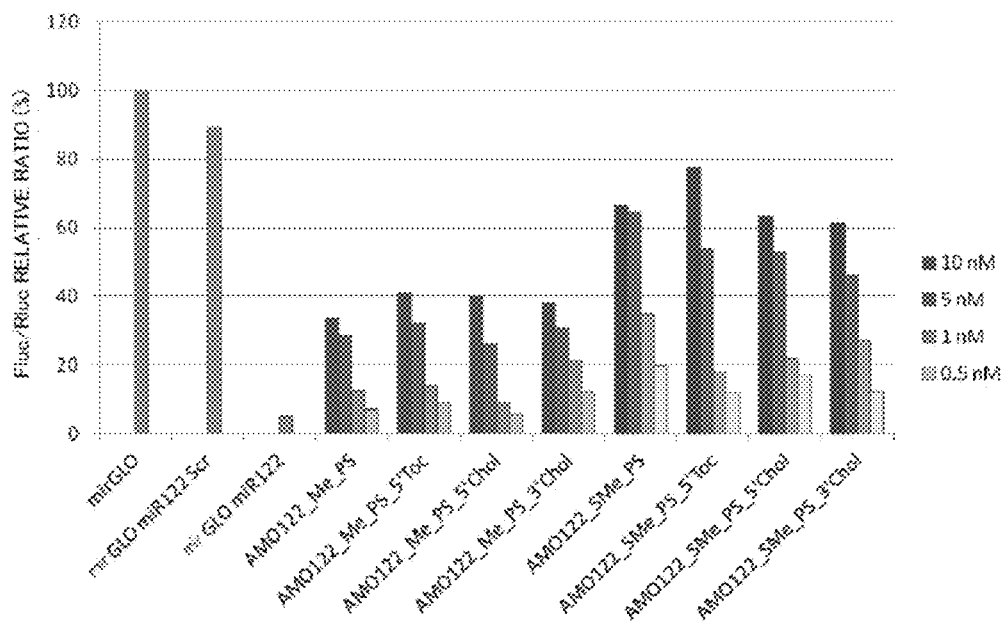
FIG. 10 is a graph depicting inhibitory effects of conjugated AMOs 122 on miRNA-122 (after 24 hours from co-transfection)
Figure 11:
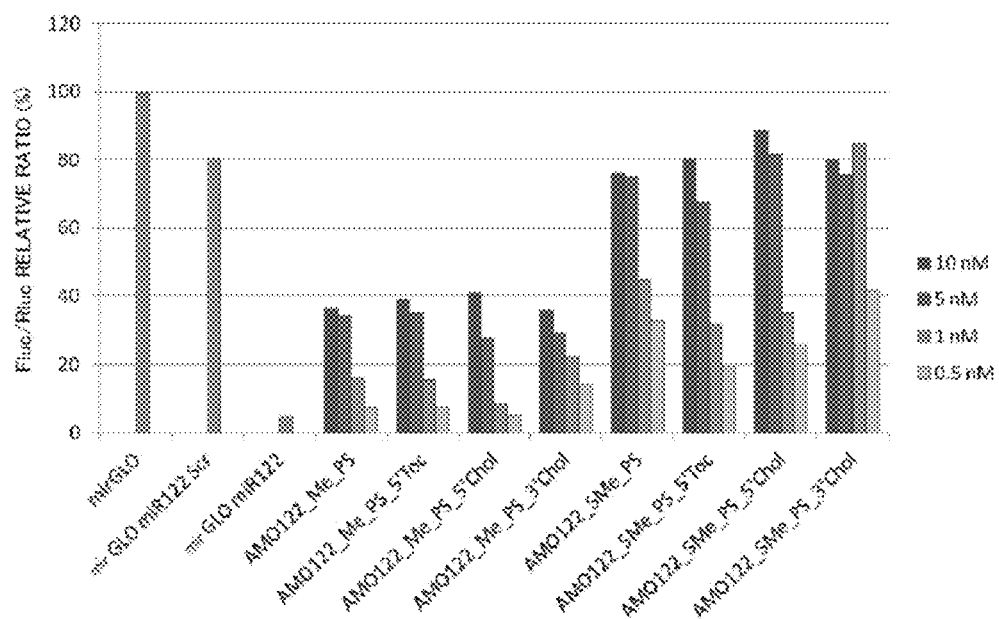
FIG. 11 is a graph depicting inhibitory effects of the conjugated AMOs 122 on miRNA-122 (after 48 hours from co-transfection)
Figure 12:
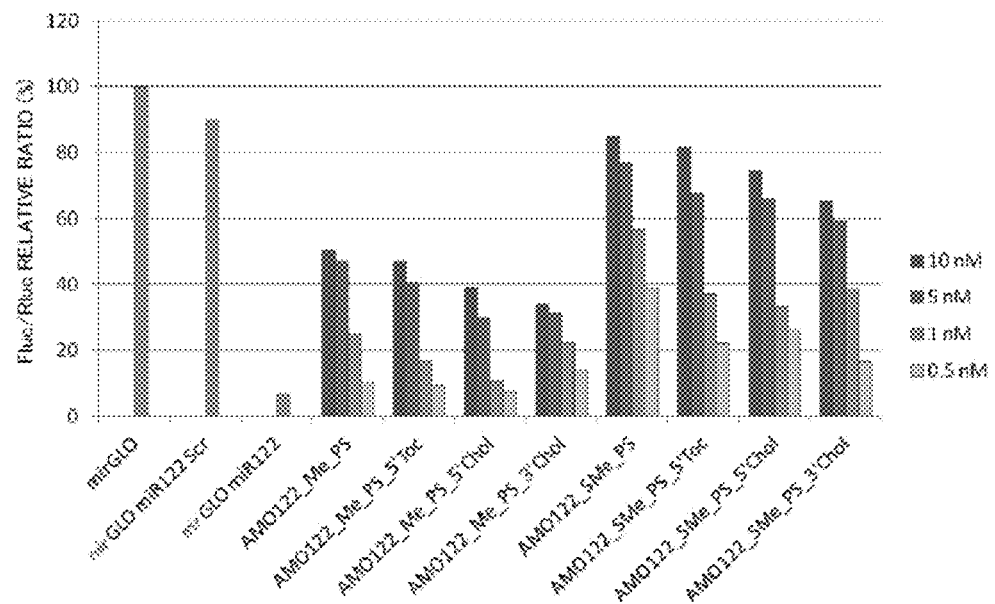
FIG. 12 is a graph depicting inhibitory effects of the conjugated AMOs 122 on miRNA-122 (after 72 hours from co-transfection)

FIG. 10 indicates results obtained after 24 hours from the co-transfection; FIG. 11 indicates results obtained after 48 hours therefrom; and FIG. 12 indicates results obtained after 72 hours therefrom. In FIGS. 10 to 12, the concentrations of the individual AMOs are 10 nM, 5 nM, 1 nM, and 0.5 nM in order from the left of the four columns of the individual AMOs.

In FIGS. 10 to 12, as compared to the Comparative Examples AMO122_Me_PS_5'Toc, AMO122_Me_PS_5'Chol, and AMO122_Me_PS_3'Chol, the Fluc/Rluc relative ratio was shown to be dose-dependently higher in AMO122_SMe_PS_5'Toc, AMO122_SMe_PS_5'Chol, and AMO122_SMe_PS_3'Chol, where the relative ratios thereof in the AMOs were approximately at the same level as that in the unconjugated AMO122_SMe_PS. The results showed that the conjugated AMOs according to the Example of the present invention inhibit miRNA, as with the unconjugated AMOs.

Example 4

Analysis by Real-Time PCR Method

AMO122_SMe_PS or AMO122_Me_PS as Comparative Example, respectively, was transfected in Huh-7 cells and then, the expression level of miRNA-122 after 48 hours from the transfection was quantified by a real-time PCR method.

The procedures of the real-time PCR will be described below.

The Huh-7 cells were cultured in a Dulbecco's modified Eagle's medium (DMEM) (Gibco, Inc) (containing 10% fetal bovine serum (FBS), 100 units/mL$^{-1}$ penicillin, and 100 μg/mL$^{-1}$ streptomycin) at 37° C. in 5% $CO_2$ in air.

In DMEM (Sigma, Inc) (containing 10% FBS (Thermo Fisher Scientific, Inc), 100 units/mL$^{-1}$ penicillin, and 100 μg/mL$^{-1}$ streptomycin), the cells were seeded at a density of $1.5 \times 10^5$ cells in each well of a 6-well plate. Twenty-four hours later, AMO122_SMe_PS or AMO122_Me_PS was transfected using LIPOFECTAMINE 2000 (purchased from Invitrogen, Inc.) in accordance with an attached instruction manual and incubated at 37° C. At that time, Opti-MEM (purchased from Invitrogen, Inc) was used as culture medium. After 6 hours from the transfection, the medium was replaced by a complete medium (DMEM as mentioned above), and again incubation was performed at 37° C. After 48 hours from the transfection, the cells were washed with PBS and then QIAzol Lysis Reagent (Qiagen, Inc) was added to dissolve the cells. The obtained solution was purified using miRNeasy Mini Kit (Qiagen, Inc.) to extract total RNA.

Using 10 ng of the extracted RNA sample, reverse transcription reaction was performed. The reverse transcription reaction was performed using miRNA-122 specific RT primers of TaqMan (registered trade mark) Small RNA Assays (Applied biosystems, Inc) and a TaqMan (registered trademark) MicroRNA Reverse Transcription Kit (Applied Biosystems, Inc.) (at 16° C. for 30 minutes, at 42° C. for 30 minutes, and at 85° C. for 5 minutes).

An amount of 1.33 μl, of the reverse transcription reaction solution obtained above, 1.0 μL of TaqMan (registered trade mark) Small RNA Assays (a mixture of an miRNA-122 specific forward primer, an miRNA-122 specific reverse primer, and an miRNA-122 specific TaqMan (registered trademark) MGB probe) (Applied biosystems, Inc), and 10 μl, of TaqMan Universal PCR Master Mix II (Applied biosystems, Inc) were mixed together to measure the expression level of miRNA-122 in the cells by a real-time PCR method. The real-time PCR used LightCycler (registered trademark) 480 Real-Time PCR System (Roche Applied Science, Inc) was used to perform one cycle at 50° C. for 2 minutes, one cycle at 95° C. for 10 minutes, and 40 cycles at 95° C. for 15 seconds and 60° C. for 1 minute. At that time, the expression level of RNU6B as an internal standard gene was used to standardize the expression level of miRNA-122.

Figure 13:
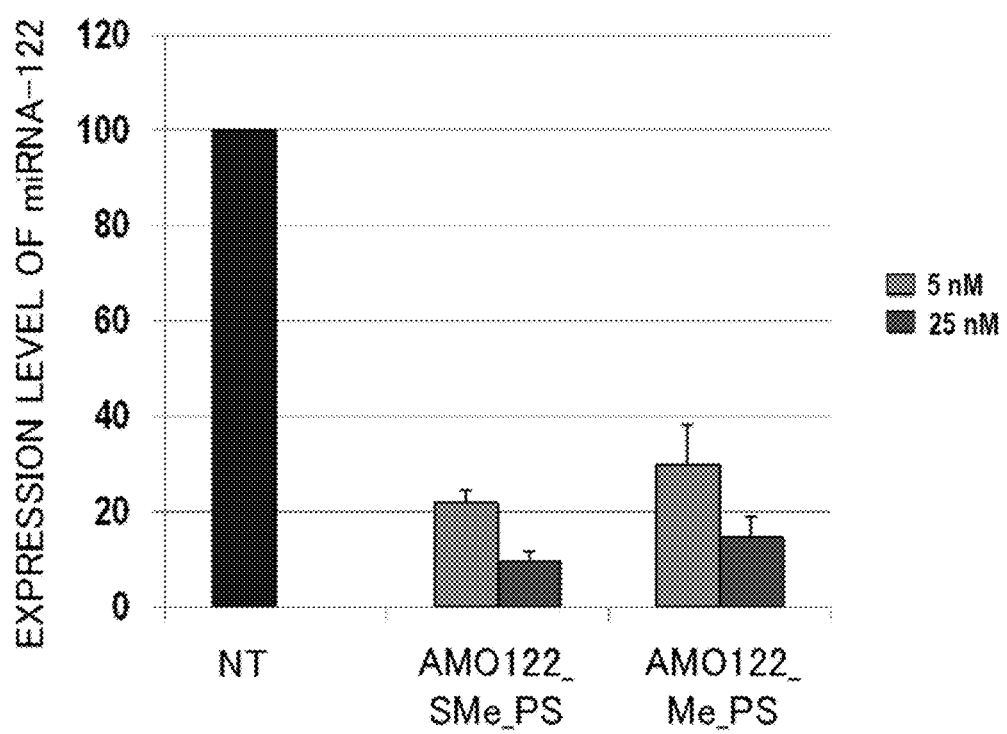
FIG. 13 is a graph depicting inhibitory effects of AMO122_SMe_PS on miRNA-122 (after 48 hours from transfection) (Real-Time PCR Method).

FIG. 13 indicates the results. In FIG. 13, when the expression level of miRNA-122 in the "NT" (non-treated: non-treated cells) is set as 100, the expression levels of miRNA 122 in the cells are indicated by the proportion of expression level of miRNA-122 in each AMO with respect to the "NT". In addition, the concentrations of the each AMO are 5 nM and 25 nM in order from the left of the two columns of the each AMO.

As compared to the Comparative Example AMO122_Me_PS, the expression level of miRNA-122 in AMO122_SMe_PS was inhibited at lower levels. In addition, the inhibition of miRNA expression level was dose-dependent. Accordingly, the quantification by the real-time PCR method also showed that the AMO 122 according to the Example of the present invention inhibits miRNA-122.

As described hereinabove, the oligonucleotide derivative according to the present invention has excellent effect persistence durable in use in vivo and thermal stability and therefore can efficiently regulate miRNA function.

Various embodiments and modifications are available to the present invention without departing from the broad sense of spirit and scope of the invention. In addition, the embodiments described above are merely illustrative of the present invention and not to be construed as limiting the invention. In other words, the scope of the present invention is set forth by the appended claims, not by the embodiments, and various modifications that come within the scope of the claims and the scope of significance of the invention equivalent thereto are considered to be within the scope of the invention.

The present invention is based on Japanese Patent Application No. 2011-125734 filed on Jun. 3, 2011, and the entire specification, scope of claims, and drawings of which are incorporated herein by reference.

The invention claimed is:

1. A method for treatment comprising administering an oligonucleotide derivative comprising repeating structural units represented by general formula:

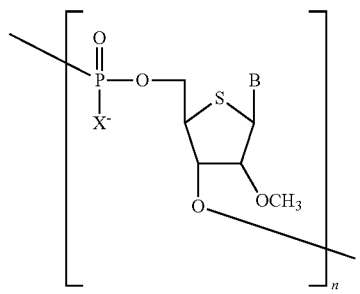

wherein B represents adenine, guanine, cytosine, or uracil; X represents a sulfur atom in all of the repeating structural units represented by the general formula; n represents an integer of 6 to 60; and B and X are independently represented in each of the repeating structural units, wherein the oliqonucleotide derivative comprises a sequence complementary to an entire sequence or a partial sequence of a miRNA.

2. The method according to claim 1, wherein at least one ligand is bound to the 5' end, the 3' end, or both the 5' end and the 3' end of the oligonucleotide derivative.

3. The method according to claim 1, wherein the oligonucleotide derivative comprises a sequence complementary to the entire sequence or a partial sequence of a miRNA.

4. The method according to claim 3, wherein the miRNA is miRNA-21.

5. The method according to claim 3, wherein the miRNA is miRNA-122.

6. A method for diagnosis comprising administering an oligonucleotide derivative comprising repeating structural units represented by general formula:

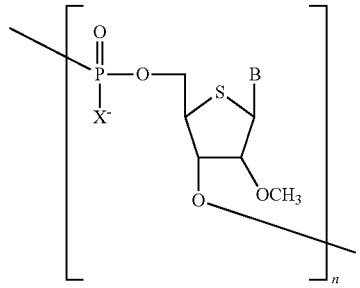

wherein B represents adenine, guanine, cytosine, or uracil; X represents a sulfur atom in all of the repeating structural units represented by the general formula; n represents an integer of 6 to 60; and B and X are independently represented in each of the repeating structural units, wherein the oligonucleotide derivative comprises a sequence complementary to an entire sequence or a partial sequence of a miRNA.

7. A method for inhibiting miRNA function comprising administering an oligonucleotide derivative comprising repeating structural units represented by general formula:

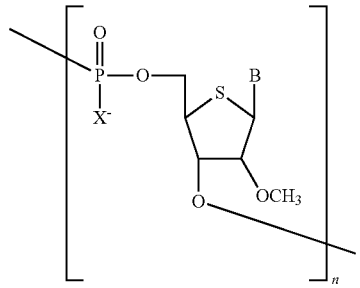

wherein B represents adenine, guanine, cytosine, or uracil; X represents a sulfur atom in all of the repeating structural units represented by the general formula; n represents an integer of 6 to 60; and B and X are independently represented in each of the repeating structural units, wherein the oliqonucleotide derivative comprises a sequence complementary to an entire sequence or a partial sequence of a miRNA.

* * * * *

SEQUENCE LISTING

```
<160> NUMBER OF SEQ ID NOS: 7

<210> SEQ ID NO 1
<211> LENGTH: 22
<212> TYPE: RNA
<213> ORGANISM: Homo sapiens

<400> SEQUENCE: 1
uagcuuauca gacugauguu ga                                                  22

<210> SEQ ID NO 2
<211> LENGTH: 23
<212> TYPE: RNA
<213> ORGANISM: Homo sapiens

<400> SEQUENCE: 2
uggaguguga caaugguguu ugu                                                 23

<210> SEQ ID NO 3
<211> LENGTH: 22
<212> TYPE: RNA
<213> ORGANISM: Artificial
<220> FEATURE:
<223> OTHER INFORMATION: Antisense RNA

<400> SEQUENCE: 3
ucaacaucag ucugauaagc ua                                                  22

<210> SEQ ID NO 4
<211> LENGTH: 32
<212> TYPE: RNA
<213> ORGANISM: Artificial
<220> FEATURE:
<223> OTHER INFORMATION: Antisense RNA

<400> SEQUENCE: 4
ucuuaucaac aucagucuga uaagcuaacc uu                                       32

<210> SEQ ID NO 5
<211> LENGTH: 23
<212> TYPE: RNA
<213> ORGANISM: Artificial
<220> FEATURE:
<223> OTHER INFORMATION: Antisense RNA

<400> SEQUENCE: 5
acaaacacca uugucacacu cca                                                 23

<210> SEQ ID NO 6
<211> LENGTH: 22
<212> TYPE: DNA
<213> ORGANISM: Artificial
<220> FEATURE:
<223> OTHER INFORMATION: Synthetic oliogonucleotide complementary to
      miRNA-21
```

```
<400> SEQUENCE: 6
tcaacatcag tctgataagc ta                                      22

<210> SEQ ID NO 7
<211> LENGTH: 23
<212> TYPE: DNA
<213> ORGANISM: Artificial
<220> FEATURE:
<223> OTHER INFORMATION: Synthetic oliogonucleotide complementary to
      miRNA-122

<400> SEQUENCE: 7
acaaacacca ttgtcacact cca                                     23
```